(12) United States Patent
Yang et al.

(10) Patent No.: US 11,166,124 B2
(45) Date of Patent: Nov. 2, 2021

(54) CONTEXT-BASED MANAGEMENT OF WEARABLE COMPUTING DEVICES

(71) Applicant: Intel Corporation, Santa Clara, CA (US)

(72) Inventors: Xue Yang, San Jose, CA (US); Steven T. Holmes, Redwood City, CA (US)

(73) Assignee: Intel Corporation, Santa Clara, CA (US)

( * ) Notice: Subject to any disclaimer, the term of this patent is extended or adjusted under 35 U.S.C. 154(b) by 226 days.

(21) Appl. No.: 16/573,223

(22) Filed: Sep. 17, 2019

(65) Prior Publication Data

US 2020/0015042 A1 Jan. 9, 2020

Related U.S. Application Data

(62) Division of application No. 14/496,380, filed on Sep. 25, 2014, now Pat. No. 10,419,886.

(51) Int. Cl.
*H04W 4/029* (2018.01)
*H04W 4/80* (2018.01)
(Continued)

(52) U.S. Cl.
CPC ............ *H04W 4/029* (2018.02); *G06F 1/163* (2013.01); *G06F 1/1694* (2013.01);
(Continued)

(58) Field of Classification Search
CPC ... H04W 4/029; H04W 4/80; H04W 52/0209; H04W 4/02; G06F 1/163; G06F 1/1694;
(Continued)

(56) References Cited

U.S. PATENT DOCUMENTS 8,803,366 B2   8/2014  Proud
8,810,430 B2   8/2014  Proud
(Continued)

FOREIGN PATENT DOCUMENTS

CN   101529878 A   9/2009
CN   102483640 A   5/2012
(Continued)

OTHER PUBLICATIONS

European Patent Office, "Communication Under Rule 71(3) EPC," issued in connection with European Patent Application No. 15844589.0, dated Sep. 21, 2020, 44 pages.
(Continued)

*Primary Examiner* — Christopher M Brandt
(74) *Attorney, Agent, or Firm* — Hanley, Flight & Zimmerman, LLC

(57) ABSTRACT

Technologies for context-based management of wearable computing devices include a mobile computing device and a wearable computing device. The wearable computing device generates sensor data indicative of a location context of the wearable computing device and transmits the sensor data to the mobile computing device. The mobile computing device generates local sensor data indicative of a location context of the wearable computing device and fuses the local sensor data with the sensor data received from the wearable computing device. The mobile computing device determines a context of the wearable computing device based on the fused sensor data. The mobile computing device determines whether an adjustment to the functionality of the wearable computing device is required based on the determined context. The mobile computing device manages the functionality of the wearable computing device in response to determining that an adjustment to the functionality is required.

29 Claims, 6 Drawing Sheets

(51) Int. Cl.

| | | |
|---|---|---|
| G06F 1/16 | (2006.01) | |
| G06F 1/3206 | (2019.01) | |
| G06F 1/3234 | (2019.01) | |
| H04Q 9/00 | (2006.01) | |
| G08C 17/02 | (2006.01) | |
| A61B 5/11 | (2006.01) | |
| A61B 5/00 | (2006.01) | |
| H04W 52/02 | (2009.01) | |

(52) U.S. Cl.
CPC .......... *G06F 1/3206* (2013.01); *G06F 1/3234* (2013.01); *G08C 17/02* (2013.01); *H04Q 9/00* (2013.01); *H04W 4/80* (2018.02); *A61B 5/1112* (2013.01); *A61B 5/1113* (2013.01); *A61B 5/6801* (2013.01); *G08C 2201/93* (2013.01); *H04Q 2209/40* (2013.01); *H04W 52/0209* (2013.01)

(58) Field of Classification Search
CPC ....... G06F 1/3206; G06F 1/3234; H04Q 9/00; H04Q 2209/40; G08C 17/02; G08C 2201/93; A61B 5/1112; A61B 5/1113; A61B 5/6801
See application file for complete search history.

(56) References Cited

U.S. PATENT DOCUMENTS

| | | | |
|---|---|---|---|
| 8,850,421 B2 | 9/2014 | Proud | |
| 9,055,791 B2 | 6/2015 | Proud et al. | |
| 9,149,189 B2 | 10/2015 | Proud | |
| 9,159,223 B2 | 10/2015 | Proud | |
| 9,204,798 B2 | 12/2015 | Proud | |
| 10,419,886 B2 | 9/2019 | Yang et al. | |
| 2001/0022558 A1* | 9/2001 | Karr, Jr. ................... | G01S 1/028 342/450 |
| 2007/0075965 A1 | 4/2007 | Huppi et al. | |
| 2009/0189810 A1* | 7/2009 | Murray .................... | G01S 19/48 342/357.31 |
| 2011/0018794 A1 | 1/2011 | Linsky et al. | |
| 2013/0214967 A1* | 8/2013 | Shin ........................ | G01S 19/34 342/357.3 |
| 2013/0227179 A1 | 8/2013 | Kalayjian et al. | |
| 2013/0278076 A1 | 10/2013 | Proud | |
| 2013/0281801 A1 | 10/2013 | Proud | |
| 2013/0283256 A1 | 10/2013 | Proud | |
| 2013/0285836 A1 | 10/2013 | Proud | |
| 2013/0290427 A1 | 10/2013 | Proud | |
| 2014/0045463 A1 | 2/2014 | Hsieh et al. | |
| 2014/0045480 A1 | 2/2014 | Hsieh et al. | |
| 2014/0045547 A1 | 2/2014 | Singamsetty et al. | |
| 2014/0106677 A1 | 4/2014 | Altman | |
| 2014/0180968 A1 | 6/2014 | Song et al. | |
| 2014/0201517 A1* | 7/2014 | Corrion ................. | H04W 12/06 713/155 |
| 2014/0218184 A1* | 8/2014 | Grant ....................... | G08B 6/00 340/407.1 |
| 2014/0245783 A1 | 9/2014 | Proud et al. | |
| 2014/0245784 A1 | 9/2014 | Proud et al. | |
| 2014/0245785 A1 | 9/2014 | Proud et al. | |
| 2014/0245786 A1 | 9/2014 | Proud et al. | |
| 2014/0245787 A1 | 9/2014 | Proud et al. | |
| 2014/0245788 A1 | 9/2014 | Proud et al. | |
| 2014/0245789 A1 | 9/2014 | Proud et al. | |
| 2014/0245790 A1 | 9/2014 | Proud et al. | |
| 2014/0245791 A1 | 9/2014 | Proud et al. | |
| 2014/0246497 A1 | 9/2014 | Proud et al. | |
| 2014/0246498 A1 | 9/2014 | Proud et al. | |
| 2014/0246499 A1 | 9/2014 | Proud et al. | |
| 2014/0246500 A1 | 9/2014 | Proud et al. | |
| 2014/0246501 A1 | 9/2014 | Proud et al. | |
| 2014/0246917 A1 | 9/2014 | Proud et al. | |
| 2014/0246924 A1 | 9/2014 | Proud | |
| 2014/0247134 A1 | 9/2014 | Proud | |
| 2014/0247135 A1 | 9/2014 | Proud | |
| 2014/0247136 A1 | 9/2014 | Proud et al. | |
| 2014/0247140 A1 | 9/2014 | Proud | |
| 2014/0247141 A1 | 9/2014 | Proud | |
| 2014/0247142 A1 | 9/2014 | Proud | |
| 2014/0247143 A1 | 9/2014 | Proud | |
| 2014/0247144 A1 | 9/2014 | Proud | |
| 2014/0247145 A1 | 9/2014 | Proud | |
| 2014/0247146 A1 | 9/2014 | Proud | |
| 2014/0247147 A1 | 9/2014 | Proud | |
| 2014/0247148 A1 | 9/2014 | Proud | |
| 2014/0247149 A1 | 9/2014 | Proud | |
| 2014/0247150 A1 | 9/2014 | Proud | |
| 2014/0247151 A1 | 9/2014 | Proud et al. | |
| 2014/0247152 A1 | 9/2014 | Proud | |
| 2014/0247153 A1 | 9/2014 | Proud | |
| 2014/0247154 A1 | 9/2014 | Proud | |
| 2014/0247155 A1 | 9/2014 | Proud | |
| 2014/0247156 A1 | 9/2014 | Proud | |
| 2014/0249379 A1 | 9/2014 | Proud | |
| 2014/0249393 A1 | 9/2014 | Proud | |
| 2014/0249760 A1 | 9/2014 | Proud et al. | |
| 2014/0249825 A1 | 9/2014 | Proud | |
| 2014/0249852 A1 | 9/2014 | Proud | |
| 2014/0249853 A1 | 9/2014 | Proud et al. | |
| 2014/0249994 A1 | 9/2014 | Proud | |
| 2014/0250181 A1 | 9/2014 | Proud | |
| 2014/0250430 A1 | 9/2014 | Proud | |
| 2015/0178362 A1* | 6/2015 | Wheeler ................. | G06F 16/27 707/639 |
| 2015/0185874 A1* | 7/2015 | Raffa .................... | G06F 3/0346 345/158 |
| 2015/0187206 A1* | 7/2015 | Saurin .................... | G08C 17/02 340/5.61 |
| 2015/0230022 A1* | 8/2015 | Sakai .................... | H04R 1/1041 381/58 |
| 2015/0282759 A1* | 10/2015 | Lin ........................ | G16H 20/30 600/301 |
| 2015/0296480 A1* | 10/2015 | Kinsey ................ | H04M 19/047 455/41.3 |
| 2016/0003623 A1* | 1/2016 | Venkatraman ......... | G01C 21/20 701/410 |
| 2016/0065727 A1* | 3/2016 | Yeon ................. | H04M 1/72412 455/556.1 |
| 2016/0094936 A1 | 3/2016 | Yang et al. | |
| 2016/0198319 A1* | 7/2016 | Huang .................... | H04L 67/26 455/412.2 |
| 2017/0010658 A1* | 1/2017 | Tanaka .................... | G06F 3/011 |

FOREIGN PATENT DOCUMENTS

| | | |
|---|---|---|
| CN | 103970208 A | 8/2014 |
| EP | 3090417 A1 | 11/2016 |
| WO | 2012141811 A1 | 10/2012 |
| WO | 20140062714 A1 | 4/2014 |
| WO | 2014137918 A1 | 9/2014 |
| WO | 2015127070 A1 | 8/2015 |

OTHER PUBLICATIONS

Chinese Patent Office, "Notification to Grant Patent Right," issued in connection with Chinese Patent Application No. 201580045442, dated Nov. 5, 2020, 4 pages (includes English translation).
Chinese Office action in Chinese patent application No. 201580045442. 0, dated Oct. 9, 2019, including machine translation (19 pages).
Chinese Office action in Chinese patent application No. 201580045442. 0, dated Aug. 12, 2020, including machine translation (6 pages).
International Searching Authority, "International Search Report," issued in connection with International Patent Application No. PCT/US2015/046543, dated Dec. 23, 2015, 4 pages.
International Searching Authority, "Written Opinion," issued in connection with International Patent Application No. PCT/US2015/046543, dated Dec. 23, 2015, 7 pages.
European Patent Office, "Search Report," issued in connection with European Patent Application No. 15844589.0, dated Apr. 4, 2018, 10 pages.

(56) References Cited

OTHER PUBLICATIONS

European Patent Office, "Communication pursuant to Article 94(3) EPC" issued in connection with European Patent Application No. 15844589.0, dated Jan. 17, 2019, 8 pages.
The International Bureau, "International Preliminary Report on Patentability," issued in connection with International Patent Application No. PCT/US2015/046543, dated Mar. 28, 2017, 8 pages.
European Patent Office, "Decision to Grant a European Patent Pursuant to Article 97(1) EPC," issued in connection with European Patent Application No. 15844589.0, dated Jan. 28, 2021, 2 pages.
The State Intellectual Property Office of People's Republic of China, "First Office Action," issued in connection with application No. 201580045442.0, dated Feb. 1, 2019, 28 pages (includes English machine translation).
United States Patent and Trademark Office, "Non-Final Office Action," issued in connection with U.S. Appl. No. 14/496,380, dated Jul. 26, 2018, 10 pages.
United States Patent and Trademark Office, "Restriction," issued in connection with U.S. Appl. No. 14/496,380, dated Jun. 16, 2017, 4 pages.
United States Patent and Trademark Office, "Final Office Action," issued in connection with U.S. Appl. No. 14/496,380, dated Jan. 2, 2019, 9 pages.
United States Patent and Trademark Office, "Notice of Allowance," issued in connection with U.S. Appl. No. 14/496,380, dated May 2, 2019, 10 pages.
United States Patent and Trademark Office, "Corrected Notice of Allowability," issued in connection with U.S. Appl. No. 14/496,380, dated Jun. 21, 2019, 7 pages.
European Patent Office, "Communication pursuant to Article 94(3) EPC" issued in connection with European Patent Application No. 15844589.0, dated Sep. 3, 2019, 4 pages.
Chinese Office action in Chinese patent application No. 201580045442. 0, dated Mar. 24, 2020, including machine translation (21 pages).

\* cited by examiner

CONTEXT-BASED MANAGEMENT OF WEARABLE COMPUTING DEVICES

CROSS-REFERENCE TO RELATED APPLICATIONS

This patent arises from a divisional of U.S. patent application Ser. No. 14/496,380, entitled "CONTEXT-BASED MANAGEMENT OF WEARABLE COMPUTING DEVICES," which was filed on Sep. 25, 2014 and issued as U.S. Pat. No. 10,419,886 on Sep. 17, 2019. Priority to U.S. patent application Ser. No. 14/496,380 is hereby claimed.

BACKGROUND

Sensors and other monitoring devices are becoming a common companion in the everyday life of many people. In fact, many of the electrical devices utilized on a daily basis by an individual include multiple sensors. For example, many mobile computing devices, such as smartphones and tablet computers, include a plethora of sensors. Sensors are also commonly used in static electronic devices, such as consumer electronics (e.g., a "smart" televisions), access security systems, and other immobile electronic devices. Additionally, in a more recent trend, sensors have been added to wearable personal items such as "smart" clothing, watches, glasses, bracelets, and other jewelry and wearable personal items.

Depending on the type of sensor and the device or item in which it is included, a sensor may be configured to monitor various stimuli and generate sensor data indicative of various characteristics. For example, the sensors included in many mobile computing devices are oftentimes configured to generate sensor data indicative of various context parameters of the mobile computing device itself, such as the current location of the mobile computing device, characteristics of the current environment of the mobile computing device, and/or other context parameters related to the mobile computing device. Alternatively, sensors included in wearable personal items are oftentimes configured to generate sensor data indicative of a context parameter of the wearable personal item such as, the current location of the wearable personal item and/or a various context parameters of the wearer such as, the wearer's heart rate or activity level.

BRIEF DESCRIPTION OF THE DRAWINGS

The concepts described herein are illustrated by way of example and not by way of limitation in the accompanying figures. For simplicity and clarity of illustration, elements illustrated in the figures are not necessarily drawn to scale. Where considered appropriate, reference labels have been repeated among the figures to indicate corresponding or analogous elements.

DETAILED DESCRIPTION OF THE DRAWINGS

Figure 1:
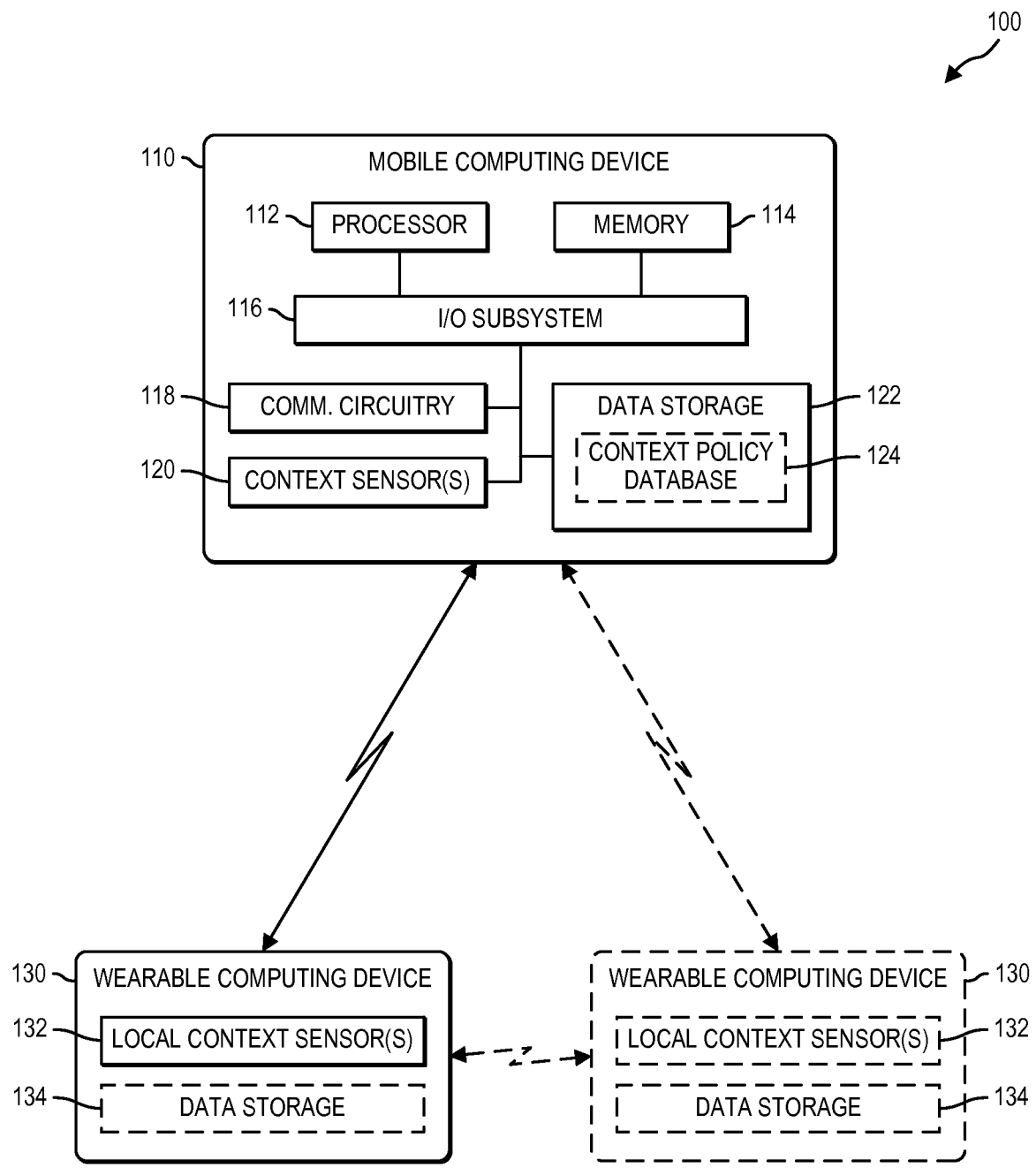
FIG. 1 is a simplified block diagram of at least one embodiment of a system for context-based management of wearable computing devices.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one of A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

The disclosed embodiments may be implemented, in some cases, in hardware, firmware, software, or any combination thereof. The disclosed embodiments may also be implemented as instructions carried by or stored on one or more transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIG. 1, in an illustrative embodiment, a system 100 for context-based control of wearable computing devices includes a mobile computing device 110 and a wearable computing device 130, which wirelessly communicate with each other. In use, context sensor(s) 120 of the mobile computing device 110 may generate sensor data indicative of a context of the mobile computing device 110 and/or a user of the mobile computing device 110. Additionally, local context sensor(s) 132 of the wearable computing device 130 may generate local sensor data indicative of a local context of the wearable computing device 130. In some embodiments, the wearable computing device 130 may transmit the local sensor data indicative of the local context to the mobile computing device 110. The mobile computing device 110 may subsequently fuse the sensor data generated by the context sensor(s) 120 with the local sensor data received from the wearable computing device 130 to generate fused sensor data. Subsequently, the mobile computing device 110 may determine a context of the wearable computing device 130 based on the fused sensor data. Thereafter, the mobile computing device 110 may compare the determined context to a context policy database 124 to determine whether an adjustment to the functionality and/or the power state of the wearable computing device 130 is required. In response to determining that an adjustment to the functionality and/or the power state of the wearable computing device 130 is required, the mobile computing device 110 may generate and transmit a management message (e.g., a control message and/or a notification message) to the wearable computing device 130. The wearable computing device 130 may adjust (e.g., modify, reconfigure, etc.) its functionality and/or power state based on the management message received from the mobile computing device 110. Additionally or alternatively, the wearable computing device 130 may display a notification message to a user of the wearable computing device 130 based on the management message received from the mobile computing device 110. It should be appreciated that by fusing the sensor data and determining the context of the wearable computing device 130 on the mobile computing device 110, the power consumption of wearable computing device 130 may be conserved.

Additionally, in some embodiments, the sensor data generated by the local context sensor(s) 132 of the wearable computing device 130 may be used to determine a more accurate location of the mobile computing device 110. In such embodiments, the context sensor(s) 120 of the mobile computing device 110 may generate sensor data indicative of a location context of the mobile computing device 110. Additionally, the local context sensor(s) 132 of the wearable computing device 130 may generate local sensor data indicative of a location context of the wearable computing device 130. The local sensor data indicative of a location context of the wearable computing device 130 may be transmitted to the mobile computing device 110. The mobile computing device 110 may fuse the sensor data indicative of the location context of the mobile computing device 110 and the received sensor data indicative of the location context of the wearable computing device 130 to generate fused location sensor data. Thereafter, the mobile computing device 110 may determine the location of the mobile computing device 110 based on the fused location sensor data. It should be appreciated that by fusing the sensor data generated by the context sensor(s) 120 with the sensor data generated by the local context sensor(s) 134 of the wearable computing device 130, a more accurate location may be determined for the mobile computing device 110.

The mobile computing device 110 may be embodied as, or otherwise include, any type of computing device capable of performing the functions described herein including, but not limited to a mobile phone, a smart phone, a tablet computing device, a personal digital assistant, a wearable computing device, a desktop computer, a laptop computing device, a server computer, a consumer electronic device, a smart television, a smart appliance, and/or other type of computing device. The illustrative mobile computing device 110 includes a processor 112, a memory 114, an input/output (I/O) subsystem 116, communication circuitry 118, one or more context sensors 120, and a data storage 122. Of course, the mobile computing device 110 may include other or additional components, such as those commonly found in a computer (e.g., various input/output devices), in other embodiments. Additionally, in some embodiments, one or more of the illustrative components may be incorporated in, or otherwise form a portion of, another component. For example, the memory 114, or portions thereof, may be incorporated in the processor 112 in some embodiments.

The processor 112 may be embodied as any type of processor capable of performing the functions described herein. For example, the processor 112 may be embodied as a single or multi-core processor(s), digital signal processor, microcontroller, or other processor or processing/controlling circuit. Similarly, the memory 114 may be embodied as any type of volatile or non-volatile memory or data storage capable of performing the functions described herein. In operation, the memory 114 may store various data and software used during operation of the mobile computing device 110 such as operating systems, applications, programs, libraries, and drivers. The memory 114 is communicatively coupled to the processor 112 via the I/O subsystem 116, which may be embodied as circuitry and/or components to facilitate input/output operations with the processor 112, the memory 114, and other components of the mobile computing device 110. For example, the I/O subsystem 116 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 116 may form a portion of a system-on-a-chip (SoC) and be incorporated, along with the processor 112, the memory 114, and other components of the mobile computing device 110, on a single integrated circuit chip.

The communication circuitry 118 of the mobile computing device 110 may be embodied as any type of communication circuit, device, or collection thereof, capable of enabling communications between the mobile computing device 110 and the wearable computing device(s) 130 and/or any other computing device. For example, the communication circuitry 118 of the mobile computing device 110 may be configured to receive sensor data transmitted by the wearable computing device(s) 130. In some embodiments, the communication circuitry 118 may be configured transmit an interrogation signal to the wearable computing device(s) 130 to promote the wearable computing device(s) 130 to transmit the sensor data. Additionally or alternatively, the communication circuitry 118 of the mobile computing device 110 may be configured to transmit management messages to the wearable computing device(s) 130 based on the determined context of the wearable computing device(s) 130. Depending on the particular type of communication modalities utilized by the wearable computing device(s) 130, the communication circuitry 118 may utilize any suitable communication protocol and related technology to effect such communication. For example, in some embodiments, the communication circuitry 118 may use the ANT+ communication protocol, the Bluetooth Low Energy (BTLE) communication protocol, or other communication protocol to communicate with the wearable computing device(s) 130.

The context sensor(s) 120 may be embodied as any type of sensors or devices capable of sensing and generating data indicative of a context of the mobile computing device 110 and/or a user of the mobile computing device 110. For example, in some embodiments, the context sensor(s) 120 may be embodied as, or otherwise include one or more location sensors. The location sensor(s) may be embodied as one or more global positioning system (GPS) sensors or devices and may be configured to determine the current location (e.g., a location context) of the mobile computing device 110. Of course, the location sensor(s) may be embodied as any other type of sensors configured to determine a location context (e.g., the current location) of the mobile computing device 110.

Additionally or alternatively, the context sensor(s) 120 may be embodied as, or otherwise include, one or more motion and/or activity sensors. In such embodiments, the motion and/or activity sensor(s) may be embodied as any type of sensor capable of sensing characteristics or parameters indicative the motion of the mobile computing device 110 or an activity being performed by a user of the mobile computing device 110. For example, the motion and/or activity sensor(s) may be embodied as one or more accelerometers, gyroscopes, magnetometers, or other sensors configured to sense various characteristics or parameters useful in determining a motion of the mobile computing device 110 or an activity of a user of the mobile computing device 110.

The context sensor(s) 120 may also be embodied as, or otherwise include, one or more environmental sensors. The environmental sensor(s) may be embodied as any type of sensor capable of sensing characteristics or parameters of the local environment of the mobile computing device 110. For example, the environmental sensor(s) may be embodied as one or more temperature sensors, light sensors, audio sensors, altitude sensors, or gas sensors. Additionally or alternatively, the environmental sensor(s) may be embodied as one or more visual sensors such as, for example, camera sensors (e.g., still camera sensors, video camera sensors, etc.) capable of capturing digital images and/or video of the local environment of the mobile computing device 110.

In some embodiments, context sensor(s) 120 may also be embodied as, or otherwise include, one or more communication sensors capable of sensing characteristics or parameters of communications between the mobile computing device 110 and the wearable computing device(s) 130. For example, in some embodiments, the communication sensor(s) may be embodied as one or more signal strength sensors configured to sense the wireless signal strength of one or more received communications from the wearable computing device(s) 130.

The data storage 122 may be embodied as any type of device or devices configured for short-term or long-term storage of data such as, for example, memory devices and circuits, memory cards, hard disk drives, solid-state drives, or other data storage devices. For example, the data storage 122 may be configured to store one or more operating systems to be initialized and/or executed by the mobile computing device 110. In some embodiments, portions of the operating system(s) may be copied to the memory 114 during operations for faster processing and/or any other reason.

In some embodiments, the data storage 122 includes a context policy database 124. The context policy database 124 includes one or more rules. Each rule may define or otherwise specify a functionality adjustment and/or a power state adjustment to be applied to the wearable computing device(s) 130 based on the context of the wearable computing device(s) 130, which as discussed in more detail below, may be determined by the mobile computing device 110 based at least in part on, or otherwise as a function of, sensor data generated by the mobile computing device 110 and sensor data generated by the wearable computing device(s) 130. In some embodiments, a rule of the context policy database 124 may define a functionality adjustment and/or a power state adjustment to be applied to a wearable computing device 130 based on a determined location (e.g., a physical location, a semantic location, etc.) of the mobile computing device 110 and/or the wearable computing device 130. For example, a rule of the context policy database 124 may specify that the functionality of a Bluetooth® headset (e.g., a wearable computing device 130) should be adjusted to provide heart rate monitoring in response to determining that the Bluetooth® headset and the mobile computing device 110 are located in a fitness facility. In another example, a different rule of the context policy database 124 may specify that the functionality of the Bluetooth® headset (e.g., the wearable computing device 130) should be adjusted to enable voice calls to be made or received in response to determining that the Bluetooth® headset and the mobile computing device 110 are located in a vehicle or a home. In yet another example, a different rule of the context policy database 124 may specify that the Bluetooth® headset (e.g., the wearable computing device 130) should be placed in a deep sleep mode in response to determining that the Bluetooth® headset is placed on a table. It should be appreciated that the rules of the context policy database 124 may define other functionality adjustments and/or power state adjustments that should be applied to the wearable computing device(s) 130 based on any other determined context.

As discussed, each rule of the context policy database 124 may define a functionality adjustment and/or a power state adjustment to be applied to the wearable computing device(s) 130 based on the determined context of the wearable computing device(s) 130 and/or the determined context of the mobile computing device 110. In some embodiments, the functionality adjustment and/or power state adjustment of one or more of the rules may be embodied as one or more instructions or commands that may be transmitted to the wearable computing device(s) 130 based on the determined context. For example, in some embodiments, a rule of the context policy database 124 may include a functionality enable instruction to cause the wearable computing device(s) 130 to initialize a function based on the determined context and/or a functionality disable instruction to cause the wearable computing device(s) 130 to terminate a function based on the determined context. In another example, the same rule or a different rule of the context policy database 124 may include a working power state instruction to cause the wearable computing device(s) 130 to enter an operational mode based on the determined context, a standby power state instruction to cause the wearable computing device(s) 130 to enter a sleep mode based on the determined context, a suspend to disk power state instruction to cause the wearable computing device(s) to enter a hibernate mode based on the determined context, and/or a shutdown power state instruction to cause the wearable computing device(s) 130 to enter a powered down mode based on the determined context.

The wearable computing device(s) 130 may be embodied as, or otherwise include, any type of computing device configured to be worn, or otherwise carried, by a user and capable of performing the functions described herein including, but not limited to, a wrist-based computing device, a smart watch, an optical head-mounted display, a headset device, a fitness tracker device, a mobile computing device, a mobile phone, a smart phone, a tablet computing device, a personal digital assistant, a consumer electronic device, a laptop computing device, a desktop computer, and/or other type of computing device. In some embodiments, the wearable computing device 130 may be embedded in, attached to, or otherwise form a part of another wearable item (e.g., a heart rate monitor embedded in a shirt or other clothing item). As such, the wearable computing device(s) 130 may include devices and structures commonly found in wearable computing devices or similar computing devices such as processors, memory devices, and communication circuitry, which are not shown in FIG. 1 for clarity of the description. In the illustrative embodiment, the wearable computing device(s) 130 include one or more local context sensors 132. In some embodiments, the wearable computing device(s) 130 also include a local data storage 134. The data storage 134 may be configured to store, among other types of data, sensor data generated by the local context sensor(s) 132 for transmission to the mobile computing device 110 at a later time.

The local context sensor(s) 132 may be embodied as any type of sensor or device capable of sensing and generating data indicative of a context of the wearable computing device(s) 130 and/or a user of the wearable computing device(s) 130. For example, the local context sensor(s) 132 may be embodied as one or more location sensors capable of determining the current location (or a location context) of the wearable computing device(s) 130. In another example, the local context sensor(s) 132 may be embodied as one or more motion and/or activity sensors capable of sensing characteristics or parameters indicative the motion of the wearable computing device(s) 130 or an activity being performed by a user of the wearable computing device(s) 130. Additionally, the local context sensor(s) 132 may be embodied as one or more environmental sensors capable of sensing characteristics or parameters of the local environment of the wearable computing device(s) 130 and/or one or more visual sensors capable of capturing digital images and/or video of the local environment of the wearable computing device(s) 130. In yet another example, the local context sensor(s) 132 may be embodied as one or more communication sensors capable of sensing characteristics or parameters of communications between the wearable computing device(s) 130 and the mobile computing device 110. It should be appreciated that such local context sensor(s) 132 may include similar structure and functionality to the corresponding context sensor(s) 120 discussed above with reference to the mobile computing device 110 and is not repeated herein for clarity of the description.

In use, the wearable computing device(s) 130 may generate sensor data indicative of a context (e.g., location context, relational context, etc.) of the wearable computing device(s) 130. The generated sensor data may be occasionally, periodically, or responsively transmitted by the wearable computing device(s) 130 to the mobile computing device 110. Additionally, in some embodiments, the wearable computing device(s) 130 may be configured to receive one or more management messages, which may be transmitted by the mobile computing device 110 based on the determined context of the wearable computing device(s) 130. The management messages may be embodied as one or more control messages and/or notification messages. In response to receiving a control message from the mobile computing device 110, the wearable computing device(s) 130 may be configured to adjust (e.g., modify, reconfigure, etc.) its current functionality and/or power state. Additionally or alternatively, the wearable computing device(s) 130 may be configured to display a notification indicative of an adjustment that should be made to its functionality or power state based on receiving a notification message from the mobile computing device 110.

Figure 2:
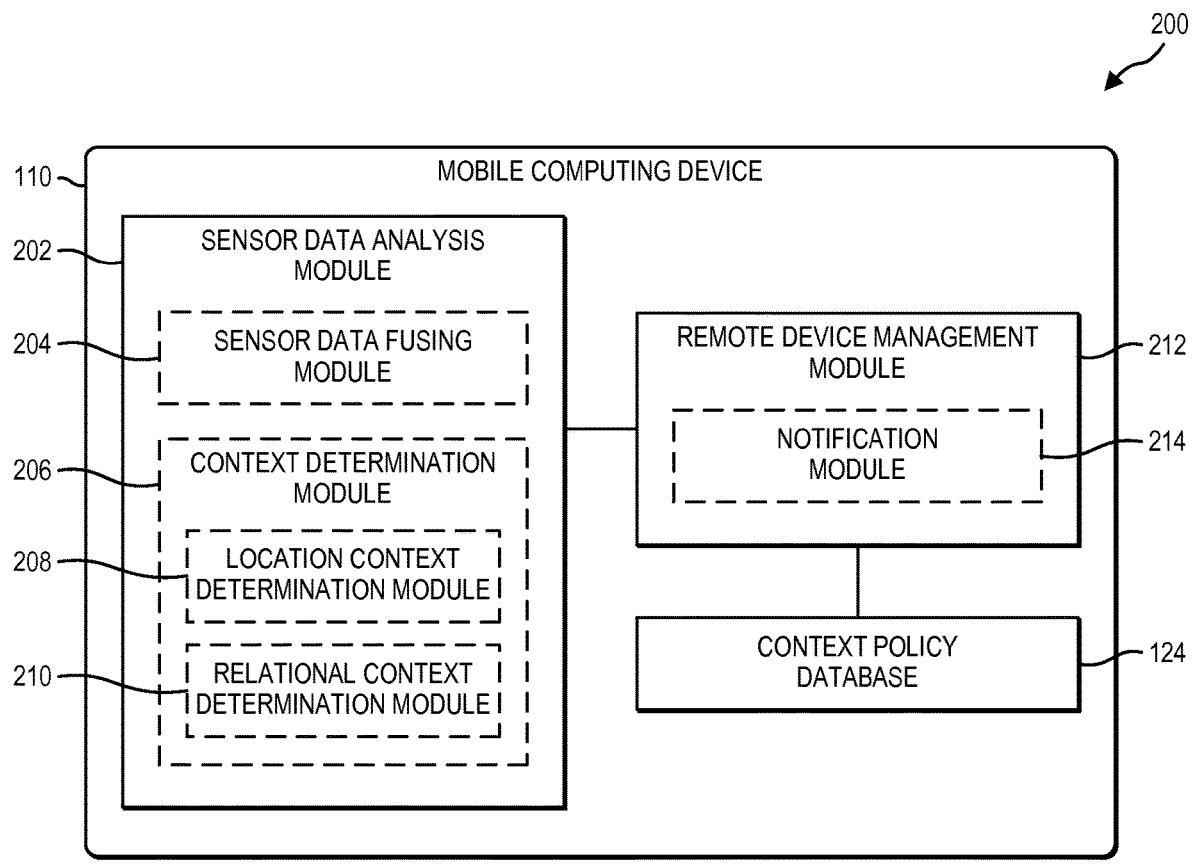
FIG. 2 is a simplified block diagram of at least one embodiment of an environment of the mobile computing devices of the system of FIG. 1.

Referring now to FIG. 2, in use, the mobile computing device establishes an environment 200 during operation. The illustrative environment 200 includes a sensor data analysis module 202 and a remote device management module 212. In some embodiments, the sensor data analysis module includes a sensor data fusing module 204 and a context determination module 206. The context determination module 206 may include a location context determination module 208 and a relational context determination module 210 in some embodiments. Additionally, the remote device management module 212 may include a notification module 214 in some embodiments. Each of the modules, logic, and other components of the environment 200 may be embodied as hardware, software, firmware, or a combination thereof. For example, each of the modules, logic and other components of the environment 200 may form a portion of, or otherwise be established by, the processor 112 or other hardware components of the mobile computing device 110. It should be appreciated that the mobile computing device 110 may include other components, sub-components, modules, and devices commonly found in a computing device, which are not illustrated in FIG. 2 for clarity of the description.

The sensor data analysis module 202 is configured to periodically or occasionally receive sensor data from the wearable computing device 130 in some embodiments. The periodicity of receiving such transmissions may be predefined in some embodiments. Additionally or alternatively, the sensor data analysis module 202 is configured to transmit an interrogation signal or other signal to the wearable computing device 130 prompting the wearable computing device 130 to transmit the sensor data in response.

In some embodiments, the sensor data received from the wearable computing device 130 may be indicative of a location context of the wearable computing device 130. For example, the sensor data received from the wearable computing device 130 may be indicative of the physical location or the absolute location (e.g., latitude, longitude, etc.) of the wearable computing device 130. Additionally or alternatively, the sensor data received from the wearable computing device 130 may be indicative of the semantic location (e.g., a home, an office, a store, a fitness facility, an automobile, a park, a living room, a kitchen, a conference room, a cubicle, a cafeteria, a hiking trail, a highway, a city street, etc.) of the wearable computing device 130.

The sensor data analysis module 202 may also receive sensor data indicative of other contexts of the wearable computing device 130 based on the particular type of local context sensor(s) 132 included in the wearable computing device 130. For example, in some embodiments, the sensor data analysis module 202 may receive sensor data indicative of a wireless signal strength between the wearable computing device 130 and another wearable computing device 130. Such sensor data may be indicative of the relative distance between the wearable computing device 130 and the other wearable computing device 130. Additionally or alternatively, the sensor data analysis module 202 may receive sensor data indicative the identity of other wearable computing devices 130 in proximity to and/or in communication with the wearable computing device 130. Such sensor data may be indicative a relational context between the wearable computing device 130 and another wearable computing device 130.

In some embodiments, the sensor data analysis module 202 is configured to fuse the sensor data received from the wearable computing device 130 with sensor data generated by the context sensor(s) 120 of the mobile computing device 110. To do so, the sensor data analysis module 202 may include the sensor data fusing module 204. The sensor data fusing module 204 may be configured to fuse, combine, or otherwise aggregate the sensor data received from the wearable computing device 130 and the sensor data generated by the context sensor(s) 120 of the mobile computing device 110 according to any suitable sensor fusing and/or combining process (e.g., Kalman filters, machine learning algorithms such as decision trees, a hidden Markov model for sequence determination, etc.). It should be appreciated that by fusing the sensor data received from the wearable computing device 130 with the sensor data generated by the context sensor(s) 120 of the mobile computing device 110, more accurate context determinations may be made concerning the wearable computing device 130 and/or the mobile computing device 110.

As discussed, in some embodiments, the sensor data analysis module 202 also includes the context determination module 206. The context determination module 206 is configured to determine the context of the wearable computing device 130 and/or the mobile computing device 110 based on the fused sensor data. In some embodiments, the context determination module 206 may include the location context determination module 208. The location context determination module 208 may be configured to determine the location context of any of the wearable computing device 130, the mobile computing device 110, and/or one or more other wearable computing devices 130 based on the fused sensor data. For example, in some embodiments, the location context determination module 208 may use the fused sensor data to determine whether the wearable computing device 130 is located in a reference location (e.g., a reference physical location and/or a reference semantic location). In another example, the location context determination module 208 may use the fused sensor data to determine whether the wearable computing device 130 is located in one reference location, determine whether the mobile computing device 110 is located in another reference location, and determine whether a different wearable computing device 130 is located in yet another reference location (e.g., a reference location different from the reference locations of the wearable computing device 130 and the mobile computing device 110).

Additionally or alternatively, the location context determination module 208 may be configured to determine a more accurate location context of the mobile computing device 110 based on the fused sensor data. As discussed, in some embodiments, the context sensor(s) 120 of the mobile computing device 110 and the local context sensor(s) 132 of the wearable computing device 130 may generate data indicative of, or otherwise for determining, the physical location (e.g., latitude, longitude, etc.) and/or the semantic location (e.g., a home, an office, a store, a fitness facility, an automobile, a park, a living room, a kitchen, a conference room, a cubicle, a cafeteria, a hiking trail, a highway, a city street, etc.) of the mobile computing device 110 and the wearable computing device 130, respectively. In such embodiments, the location context determination module 208 may use the fused location sensor data to determine the location of the mobile computing device 110. It should be appreciated that by using the fused location sensor data, a more accurate location of the mobile computing device 110 may be determined than may have been possible using only location sensor data generated by the context sensor(s) 120 of the mobile computing device 110.

Additionally, in some embodiments, the context determination module 206 includes the relational context determination module 210. The relational context determination module 210 is configured to determine the relationship between the mobile computing device 110 and the wearable computing device 130 (or multiple wearable computing devices 130) based on the fused sensor data. In such embodiments, the fused sensor data may include or otherwise be indicative of a wireless signal strength between the mobile computing device 110 and the wearable computing device(s) 130 and between each of the wearable computing device(s) 130. Additionally or alternatively, the fused sensor data may include or otherwise be indicative of the functionality of the wearable computing device(s) 130 and the mobile computing device 110, the interoperability between the mobile computing device 110 and each wearable computing device 130, and/or the particular type of each wearable computing device 130 (e.g., smart watch, fitness device, wireless communication device, etc.).

The remote device management module 212 is configured to determine whether the functionality and/or a power state of the wearable computing devices 130 needs to be adjusted based on the determined context. To do so, the remote device management module 212 compares the determined context to the context policy database 124. As discussed, the context policy database 124 includes one or more rules. Each rule of the context policy database 124 defines or otherwise specifies a functionality adjustment and/or a power state adjustment to be applied to the wearable computing device 130 based on the determined context of the wearable computing device 130. In embodiments in which the remote device management module 212 determines that an adjustment to the functionality and/or power state of the wearable computing device 130 is required, the remote device management module 212 is configured to generate one or more management messages based on the context policy database 124.

In some embodiments, one or more of the management messages generated by the remote device management module 212 includes or is otherwise embodied as one or more control messages. In such embodiments, the control message(s) include one or more functionality instructions (or commands) and/or one or more power state instructions (or commands) for causing the wearable computing device(s) 130 to adjust (e.g., modify, reconfigure, etc.) their current functionality and/or power state. For example, the one or more control messages may include a functionality enable instruction to cause the wearable computing device(s) 130 to initialize or allow initialization of a function, a functionality disable instruction to cause the wearable computing device(s) 130 to terminate or restrict initialization of a function, a working power state instruction to cause the wearable computing device 130 to enter an operational mode, a standby power state instruction to cause the wearable computing device 130 to enter a sleep mode, a suspend to disk power state instruction to cause the wearable computing device 130 to enter a hibernate mode, and/or a shutdown power state instruction to cause the wearable computing device 130 to enter a powered down mode. It should be appreciated that the control message(s) generated by the remote device management module 212 may include other or additional instructions or commands to cause the wearable computing device(s) 130 to adjust their current functionality and/or power state. In embodiments in which one or more of the management messages include or are embodied as control message(s), the remote device management module 212 is configured to transmit the control message(s) to the wearable computing device 130.

As discussed, in some embodiments, the remote device management module 212 includes the notification module 214. The notification module 214 is configured to generate a notification message to be displayed by the wearable computing device 130. In some embodiments, the notification message generated by the notification module 214 indicates to a user that adjustment to the functionality and/or the power state of the wearable computing device 130 is required. In such embodiments, the notification module 214 is configured to transmit the notification message to the wearable computing device 130.

Figure 3:
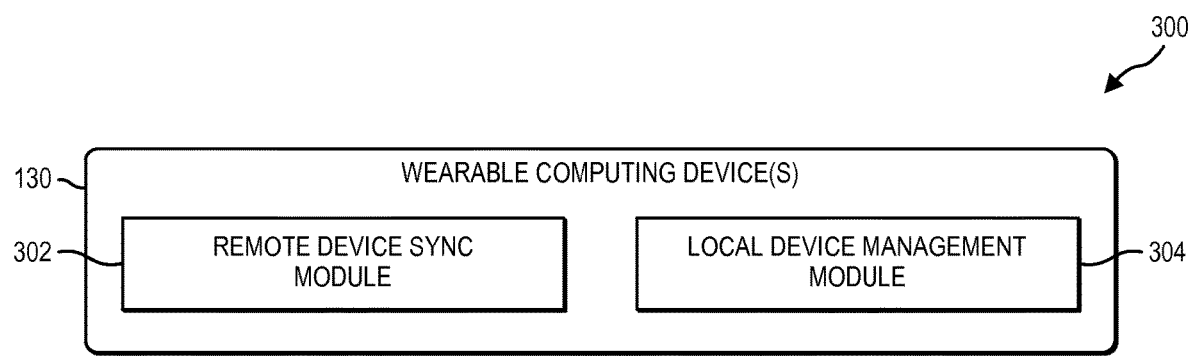
FIG. 3 is a simplified block diagram of at least one embodiment of an environment of the wearable computing devices of the system of FIG. 1.

Referring now to FIG. 3, in use, the wearable computing device 130 establishes an environment 300 during operation. The illustrative environment 300 includes a remote device synchronization module 302 and a local device management module 304. Each of the modules, logic, and other components of the environment 300 may be embodied as hardware, software, firmware, or a combination thereof. For example, each of the modules, logic and other components of the environment 300 may form a portion of, or otherwise be established by, a processor or other hardware components of the wearable computing device 130. It should be appreciated that the wearable computing device 130 may include other components, sub-components, modules, and devices commonly found in a wearable or portable computing device, which are not illustrated in FIG. 3 for clarity of the description. Additionally, as discussed above, the mobile computing device 110 may be in communication with any number of wearable computing devices 130 in some embodiments. As such, it should be understood that although each of the wearable computing devices 130 may establish the illustrative environment 300 during operation, the following discussion of that illustrative environment 300 is described with specific reference to a single wearable computing device 130 for clarity of the description.

The remote device synchronization module 302 is configured to occasionally, periodically, or responsively transmit (e.g., send, broadcast, relay, etc.) the sensor data generated by the local context sensor(s) 132 to the mobile computing device 110. For example, in some embodiments, the remote device synchronization module 302 may be configured to periodically transmit or broadcast the sensor data to the mobile computing device based on a predefined reference interval. Additionally or alternatively, the remote device synchronization module 302 may transmit the generated sensor data in response to an interrogation signal or other signal received from the mobile computing device 110. The interrogation signal received from the mobile computing device 110 may prompt or otherwise instruct the remote device synchronization module 302 to transmit the generated sensor data. As discussed, in some embodiments, the sensor data transmitted to the mobile computing device 110 may be fused or otherwise combined with sensor data generated by the mobile computing device 110. In such embodiments, the fused data may be used by the mobile computing device 110 to determine a context of the wearable computing device 130 and/or a more accurate location of the mobile computing device 110.

The local device management module 304 is configured to determine whether a management message received from the mobile computing device 110 is embodied as or includes a control message or a notification message. As discussed, in some embodiments, one or more of the management messages transmitted by the mobile computing device 110 may be embodied as a control message having instructions (or commands) to cause the current functionality or power state of the wearable computing device 130 to be adjusted (e.g., modified, reconfigured, etc.). In such embodiments, the local device management module 304 executes the functionality and/or power state instruction(s) and/or command(s) included in the control message to effect the adjustment. Additionally or alternatively, one or more of the management messages transmitted by the mobile computing device 110 may be embodied as a notification message to indicate to a user of the wearable computing device 130 that adjustment to the functionality and/or the power state of the wearable computing devices 130 is required. In some embodiments, the local device management module 304 is configured to display the notification message to the user via a display of the wearable computing device 130.

Figure 4:
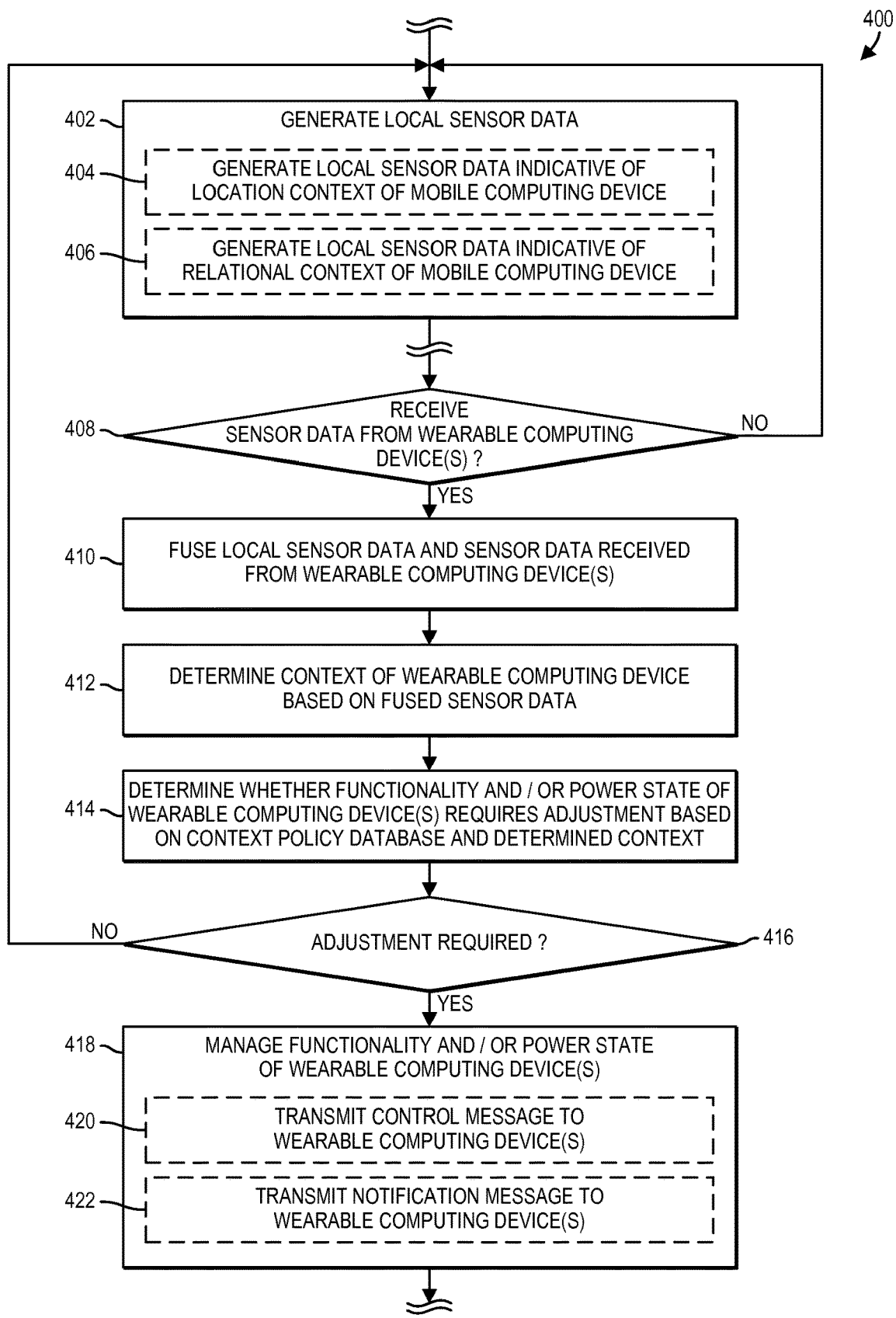
FIG. 4 is a simplified flow diagram of at least one embodiment of a method for context-based management of the wearable computing devices that may be executed by the mobile computing device of the system of FIG. 1.

Referring now to FIG. 4, in use, the mobile computing device 110 may execute a method 400 for context-based management of the wearable computing device 130. The method 400 begins with block 402 in which the context sensor(s) 120 of the mobile computing device 110 generate local sensor data. In some embodiments, in block 404, the context sensor(s) 120 may generate local sensor data indicative of a location context of the mobile computing device 110. For example, in some embodiments, the mobile computing device 110 may generate local sensor data indicative of, or otherwise for determining, the physical location or the absolute location (e.g., latitude, longitude, etc.) of the mobile computing device 110. Additionally or alternatively, the mobile computing device 110 may generate local sensor data indicative of, or otherwise for determining, the semantic location (e.g., a home, an office, a store, a fitness facility, an automobile, a park, a living room, a kitchen, a conference room, a cubicle, a cafeteria, a hiking trail, a highway, a city street, etc.) of the mobile computing device 110. Additionally or alternatively, in block 406, the context sensor(s) 120 may generate local sensor data indicative of a relational context of the mobile computing device 110. For example, in some embodiments, the context sensor(s) 120 of the mobile computing device 110 may generate local sensor data indicative of the presence of one or more wearable computing devices 130 located within a reference distance to the mobile computing device 110. Additionally or alternatively, the context sensor(s) 120 of the mobile computing device 110 may generate local sensor data indicative a wireless signal strength between the mobile computing device 110 and each of the wearable computing devices 130. The context sensor(s) 120 of the mobile computing device 110 may also generate local sensor data indicative of the interoperability and/or type of each the wearable computing devices 130. However, it should be appreciated that the particular type of local sensor data generated in block 402 may be based on the particular type of context sensor(s) 120 included in the mobile computing device 110.

In decision block 408, the mobile computing device 110 determines whether sensor data is received from the one or more wearable computing devices 130. In some embodiments, the sensor data received from the wearable computing device(s) 130 may be indicative of a location context of the wearable computing device(s) 130. For example, the sensor data received from the wearable computing device(s) 130 may be indicative of the physical location or the absolute location (e.g., latitude, longitude, etc.) of the wearable computing device(s) 130. Additionally or alternatively, the sensor data received from the wearable computing device(s) 130 may be indicative of the semantic location (e.g., a home, an office, a store, a fitness facility, an automobile, a park, a living room, a kitchen, a conference room, a cubicle, a cafeteria, a hiking trail, a highway, a city street, etc.) of the wearable computing device(s) 130. The mobile computing device 110 may also receive other types of sensor data based on the particular type of local context sensor(s) 132 included in the wearable computing device(s) 130. For example, in some embodiments, the mobile computing device 110 may receive sensor data from a wearable computing device 130 indicative of a wireless communication signal strength between the wearable computing device 130 and a different wearable computing device 130 located in proximity to the wearable computing device 130. If the mobile computing device 110 determines that local sensor data is not received from the wearable computing device(s) 130 in decision block 408, the method 400 subsequently loops back to block 402 in which the mobile computing device 110 continues generating sensor data. If, however, the mobile computing device 110 determines that sensor data is received from the wearable computing device(s) 130 in decision block 408, the method 400 advances to block 410.

In block 410, the mobile computing device 110 fuses, combines, or otherwise aggregates the sensor data received from the wearable computing device(s) 130 and the sensor data generated by the context sensor(s) 120 of the mobile computing device 110. To do so, the mobile computing device 110 uses any suitable sensor fusing and/or combining process (e.g., Kalman filters, machine learning algorithms such as decision trees, a hidden Markov model for sequence determination, etc.). It should be appreciated that by fusing the sensor data received from the wearable computing device 130 with the sensor data generated by the context sensor(s) 120 of the mobile computing device 110, the mobile computing device 110 may make more accurate determinations as to the context of the mobile computing device 110 and/or the wearable computing device(s) 130.

In block 412, the mobile computing device 110 may determine or infer a context of the wearable computing device(s) 130. As discussed above, the determination of the context of the wearable computing device(s) 130 may be based on the fused sensor data including the sensor data received from the wearable computing device(s) 130 and the sensor data generated by the context sensor(s) 120 of the mobile computing device 110. For example, in some embodiments, the mobile computing device 110 may determine the location of the wearable computing device(s) 130 based on the fused sensor data. As a further example, the mobile computing device 110 may determine the distance between the wearable computing device(s) 130 and the mobile computing device 110 and/or the distance between each of the wearable computing devices(s) 130 based on the fused sensor data. Additionally, the mobile computing device 110 may determine the distance between the wearable computing device(s) 130 and the mobile computing device 110 based on the fused sensor data. In yet another example, the mobile computing device 110 may determine the relationship between the mobile computing device 110 and more than one wearable computing device 130 based on the fused sensor data. Of course, the mobile computing device 110 may determine or infer other contexts of the wearable computing device(s) 130 based on the fused sensor data and/or other data in other embodiments.

In block 414, the mobile computing device 110 determines whether the functionality and/or a power state of the wearable computing device(s) 130 needs to be adjusted based on the determined context. To do so, the mobile computing device 110 compares the determined context to the context policy database 124. The context policy database 124 includes one or more rules. As discussed, each rule of the context policy database 124 defines or otherwise specifies a functionality adjustment and/or a power state adjustment to be applied to the wearable computing device(s) 130 based on the determined context of the wearable computing device(s) 130. For example, in some embodiments, a rule of the context policy database 124 may define a functionality adjustment and/or a power state adjustment to be applied to a wearable computing device 130 based on a determined location (e.g., a physical location, a semantic location, etc.) of the mobile computing device 110 and the wearable computing device 130. For instance, the rule may specify that a wearable computing device 130 should be placed in a sleep mode and/or enter a limited functionality mode in response to the mobile computing device 110 determining that the wearable computing device 130 is located on a table or in a drawer. In another example, a different rule of the context policy database 124 may define a functionality adjustment and/or a power state adjustment to be applied a wearable computing device 130 based on the relative locations of the wearable computing device 130 and the mobile computing device 110. For instance, the rule may specify that a wearable computing device 130 should be placed in a sleep mode and/or enter a limited functionality mode in response to the mobile computing device 110 determining that the distance between the wearable computing device 130 and the mobile computing device 110 exceeds a reference distance.

Additionally or alternatively, a rule of the context policy database 124 may define a functionality adjustment and/or a power state adjustment to be applied to a wearable computing device 130 based on the relationships and relative locations of multiple wearable computing devices 130 and the mobile computing device 110. For instance, the rule may specify that one of the wearable computing devices 130 should provide a particular set of functions (e.g., communicate with another wearable computing device 130) in response to the mobile computing device 110 determining that the distance between the wearable computing device 130 and the mobile computing device 110 exceeds a reference distance. The same or a different rule may specify that the same wearable computing device 130 should provide a different set of functions (e.g., communicate directly with the mobile computing device 110) in response to the mobile computing device 110 determining that the distance between the wearable computing device 130 and the mobile computing device 110 does not exceed the reference distance.

For example, in one specific embodiment, a user may be wearing multiple wearable computing devices 130 such as a heart rate monitoring headset and a smart watch while exercising at a fitness facility. In such embodiment, one rule of the context policy database 124 may specify that the heart rate monitoring headset should be configured to transmit or stream heart rate information to the smart watch while the user's mobile computing device 110 is located in a gym bag or a locker. The same or a different rule of the context policy database 124 may specify that the heart rate monitoring headset should instead be configured to transmit or stream the heart rate information to the user's mobile computing device 110 for more sophisticated data profiling and analysis in response to the mobile computing device 110 being removed from the gym bag or locker. It should be appreciated that the rules of the context policy database 124 may define other functionality adjustments and/or power state adjustments that should be applied to the wearable computing device(s) 130 based on any other determined context.

In decision block 416, the mobile computing device 110 determines whether an adjustment to the functionality and/or the power state of the wearable computing device(s) 130 is required based the comparison of the determined context to the context policy database 124. If the mobile computing device 110 determines in decision block 416 that an adjustment is not required, the method 400 loops back to block 402 and the mobile computing device 110 continues generating local sensor data. If, however, the mobile computing device 110 determines instead that an adjustment to the functionality of the wearable computing device(s) 130 is required, the method 400 advances to block 418.

In block 418, the mobile computing device 110 is configured to manage the functionality and/or the power state of the wearable computing device(s) 130. To do so, the mobile computing device 110 generates one or more management messages. In some embodiments, the one or more management messages may be embodied as one or more control messages. In such embodiments, the control message(s) includes one or more functionality instructions (or commands) and/or one or more power state instructions (or commands) for causing the wearable computing device(s) 130 to adjust (e.g., modify, reconfigure, etc.) their current functionality and/or power state. For example, the one or more control messages may include a functionality enable instruction to cause the wearable computing device(s) 130 to initialize a function, a functionality disable instruction to cause the wearable computing device(s) 130 to terminate a function, a working power state instruction to cause the wearable computing device 130 to enter an operational mode, a standby power state instruction to cause the wearable computing device 130 to enter a sleep mode, a suspend to disk power state instruction to cause the wearable computing device 130 to enter a hibernate mode, and/or a shutdown power state instruction to cause the wearable computing device 130 to enter a powered down mode. It should be appreciated that the control message(s) generated by the mobile computing device 110 may include any other instruction or command to cause the wearable computing device(s) 130 to adjust their current functionality and/or power state. In some embodiments, in block 420, the mobile computing device 110 transmits the control message(s) to one or more of the wearable computing devices 130.

Additionally or alternatively, the one or more management messages generated by the mobile computing device 110 may be embodied as one or more notification messages. In some embodiments, the notification message(s) generated by the mobile computing device 110 are to be displayed to a user of the wearable computing device(s) 130 to indicate to the user that adjustment to the functionality and/or a power state of the wearable computing device(s) 130 are required. In some embodiments, in block 422, the mobile computing device 110 transmits the notifications message(s) to one or more of the wearable computing devices 130 to be displayed.

Figure 5:
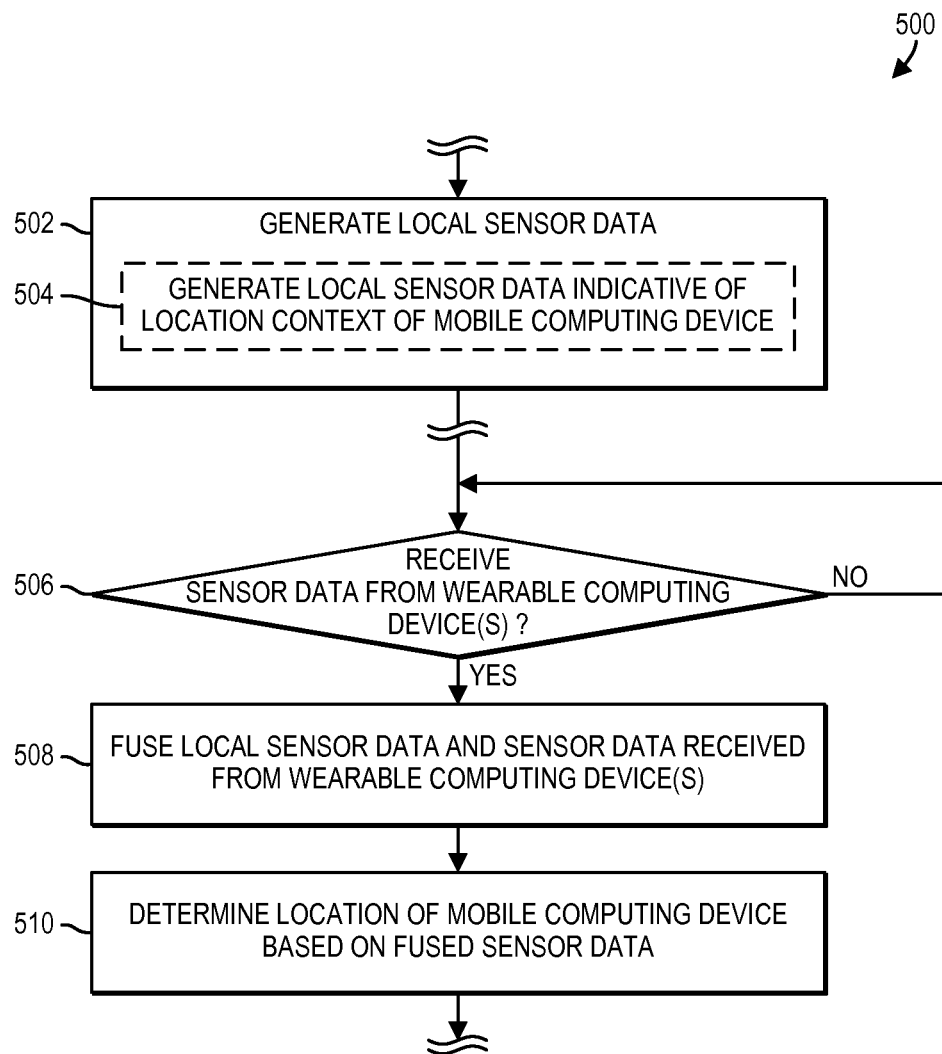
FIG. 5 is a simplified flow diagram of at least one embodiment of a method for determining a location that may be executed by the mobile computing device of the system of FIG. 1.

Referring now to FIG. 5, in use, the mobile computing device 110 may execute a method 500 for determining a location. The method 500 begins with block 502 in which the context sensor(s) 120 of the mobile computing device 110 generate local sensor data. In some embodiments, in block 504, the context sensor(s) 120 may generate local sensor data indicative of a location context of the mobile computing device 110. For example, in some embodiments, the mobile computing device 110 may generate local sensor data indicative of, or otherwise for determining, the physical location or the absolute location (e.g., latitude, longitude, etc.) of the mobile computing device 110. Additionally or alternatively, the mobile computing device 110 may generate local sensor data indicative of, or otherwise for determining, the semantic location (e.g., a home, an office, a store, a fitness facility, an automobile, a park, a living room, a kitchen, a conference room, a cubicle, a cafeteria, a hiking trail, a highway, a city street, etc.) of the mobile computing device 110. As discussed above, the particular type of local sensor data generated in block 502 may be based on the particular type of context sensor(s) 120 included in the mobile computing device 110.

In decision block 506, the mobile computing device 110 determines whether sensor data is received from the one or more wearable computing devices 130. In some embodiments, sensor data received from the wearable computing device(s) 130 may be indicative of a location context of the wearable computing device(s) 130. For example, the sensor data received from the wearable computing device(s) 130 may be indicative of the physical location or the absolute location (e.g., latitude, longitude, etc.) of the wearable computing device(s) 130. Additionally or alternatively, the sensor data received from the wearable computing device(s) 130 may be indicative of the semantic location (e.g., a home, an office, a store, a fitness facility, an automobile, a park, a living room, a kitchen, a conference room, a cubicle, a cafeteria, a hiking trail, a highway, a city street, etc.) of the wearable computing device(s) 130. As discussed above, the mobile computing device 110 may receive other types of sensor data based on the particular type of local context sensor(s) 132 included in the wearable computing device(s) 130. If the mobile computing device 110 determines that local sensor data is not received from the wearable computing device(s) 130 in decision block 506, the method 500 subsequently loops back to decision block 506 in which the mobile computing device 110 continues determining whether local sensor data is received. If, however, the mobile computing device 110 determines that local sensor data is received from the wearable computing device(s) 130 in decision block 506, the method 500 advances to block 508.

In block 508, the mobile computing device 110 fuses, combines, or otherwise aggregates the sensor data received from the wearable computing device(s) 130 and the sensor data generated by the context sensor(s) 120 of the mobile computing device 110. To do so, the mobile computing device uses any suitable sensor fusing and/or combining process (e.g., Kalman filters, machine learning algorithms such as decision trees, a hidden Markov model for sequence determination, etc.). Subsequently, the method 500 advances to block 510 in which the mobile computing device 110 may determine a current location based on the fused data. It should be appreciated that by fusing the sensor data received from the wearable computing device 130 with the sensor data generated by the context sensor(s) 120 of the mobile computing device 110, the mobile computing device 110 may make more accurate determinations as to the location of the mobile computing device 110.

Figure 6:
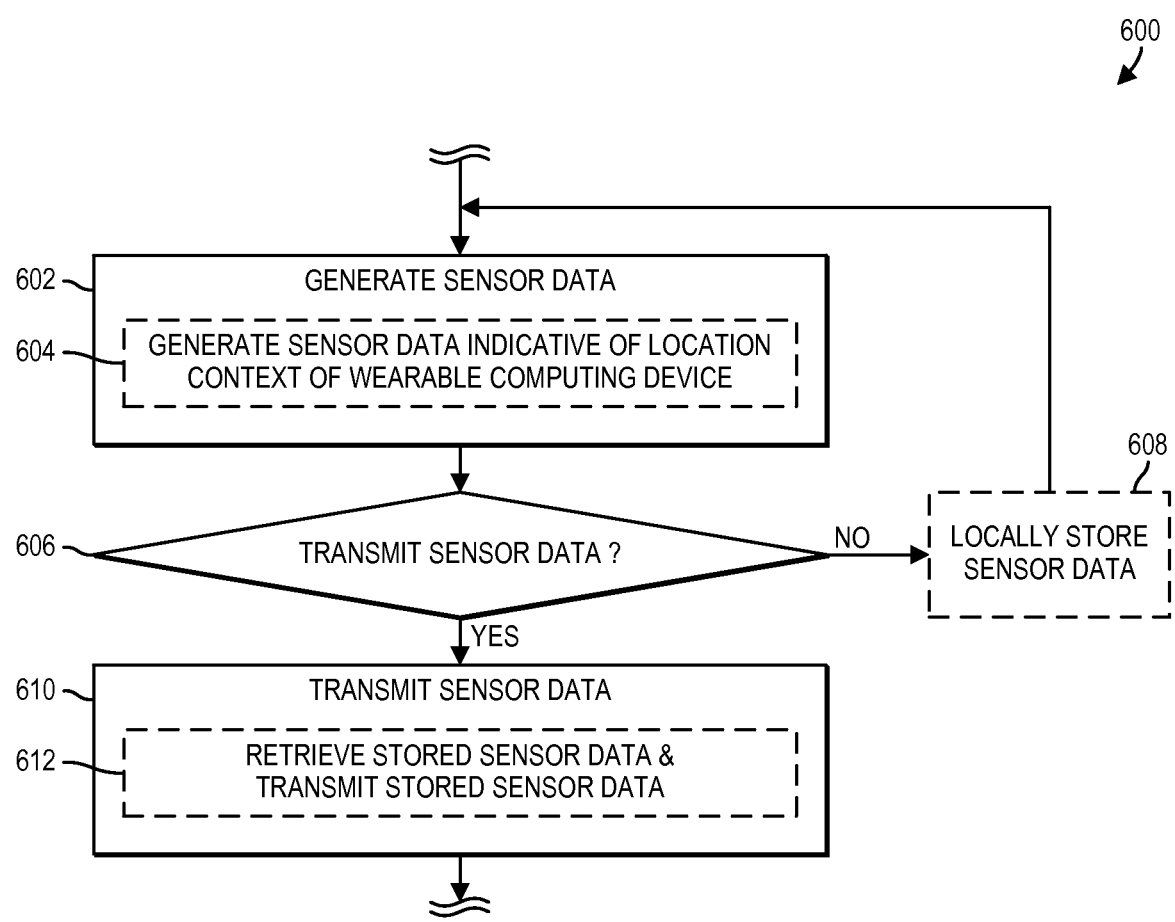
FIG. 6 is a simplified flow diagram of at least one embodiment of a method for generating and transmitting sensor data that may be executed by a wearable computing device of the system of FIG. 1.

Referring now to FIG. 6, in use, the wearable computing device 130 may execute a method 600 for generating sensor data. The method 600 begins with block 602 in which the local context sensor(s) 132 generate sensor data. In some embodiments, in block 604, the local context sensor(s) 132 may generate sensor data indicative of a location context of the wearable computing device 130. For example, in some embodiments, the wearable computing device 130 may generate sensor data indicative of, or otherwise for determining, the physical location or the absolute location (e.g., latitude, longitude, etc.) of the wearable computing device 130. Additionally or alternatively, the wearable computing device 130 may generate sensor data indicative of, or otherwise for determining, the semantic location (e.g., a home, an office, a store, a fitness facility, an automobile, a park, a living room, a kitchen, a conference room, a cubicle, a cafeteria, a hiking trail, a highway, a city street, etc.) of the wearable computing device 130. In some embodiments, the local context sensor(s) 132 may also generate other types of sensor data based on the particular type of local context sensor(s) 132 included in the wearable computing device 130. For example, in some embodiments, the local context sensor(s) 132 may generate sensor data indicative of a wireless communication signal strength between the wearable computing device 130 and a different wearable computing device 130 located in proximity to the wearable computing device 130.

In decision block 606, the wearable computing device 130 determines whether to transmit the sensor data generated in block 602 to the mobile computing device 110. As discussed above, the wearable computing device 130 may transmit the sensor data occasionally, periodically, or responsively. For example, in some embodiments, the wearable computing device 130 may be configured to periodically transmit or broadcast the sensor data. The periodicity of such transmissions may be predefined in some embodiments. Additionally or alternatively, the wearable computing device 130 may transmit the sensor data in response to an interrogation signal or other signal prompting the wearable computing device 130 to transmit the sensor data. The wearable computing device 130 may receive such an interrogation signal or other signal from the mobile computing device 110 in some embodiments.

If the wearable computing device 130 determines not to transmit the sensor data in decision block 606, the method 600 advances to block 608. In some embodiments, in block 608, the wearable computing device 130 may store the sensor data in the local data storage 134 in response to a determination not to transmit the data. In this way, the wearable computing device 130 may store sensor data over a time period and subsequently transmit an accumulation of sensor data later in time. Alternatively, in other embodiments, the wearable computing device 130 may not store the sensor data in block 608, in which case the un-transmitted sensor data may be ignored. Regardless, the method 600 subsequently loops back to block 602 in which the local context sensor(s) 132 generate additional sensor data.

Referring back to decision block 606, if the wearable computing device 130 determines that the sensor data should be transmitted, the method 600 advances to block 610 in which the wearable computing device 130 transmits the sensor data to the mobile computing device 110. As discussed above, the wearable computing device 130 may transmit the sensor data by transmitting (e.g., sending, broadcasting, relaying, etc.) the sensor data to the mobile computing device 110. In some embodiments, the wearable computing device 130 may transmit the sensor data as it is generated in real-time or near real-time. However, in embodiments in which sensor data is stored in the data storage 134, the wearable computing device 130 may retrieve the stored data from the data storage 134 and subsequently transmit the stored data in block 612. After transmission of the sensor data to the mobile computing device 110, the method 600 loops back to block 602 in which the local context sensor(s) 132 generate additional sensor data.

Figure 7:
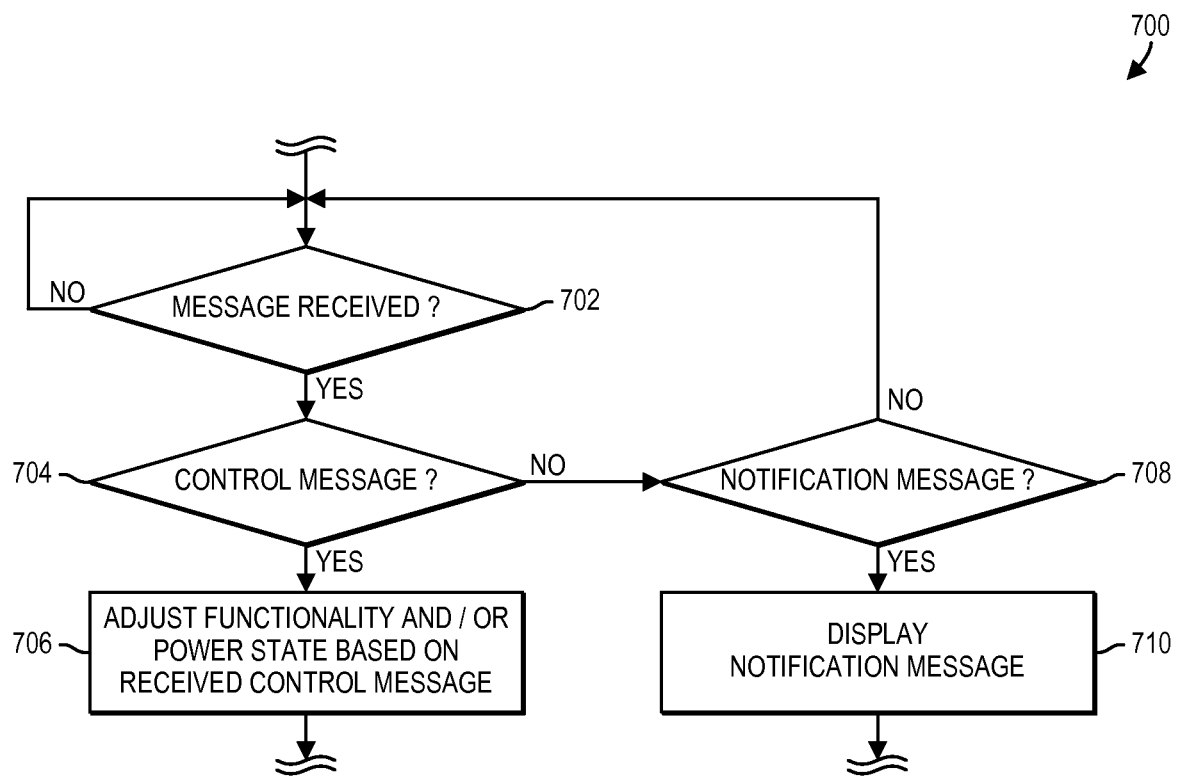
FIG. 7 is a simplified flow diagram of at least one embodiment of a method for context-based management that may be executed by a wearable computing device of the system of FIG. 1.

Referring now to FIG. 7, in use, the wearable computing device 130 may execute a method 700 for context-based control of the wearable computing device 130. The method 700 begins with decision block 702 in which the wearable computing device 130 determines whether a management message is received from the mobile computing device 110. As discussed above, the mobile computing device 110 may transmit a management message to the wearable computing device 130 in response to determining, based on the context of the wearable computing device 130, that an adjustment to the functionality and/or the current power state of the wearable computing device 130 is required. If the wearable computing device 130 determines that a management message is not received from the mobile computing device 110 in decision block 702, the method 700 subsequently loops back to decision block 702 in which the wearable computing device 130 continues determining whether a management message is received. If, however, the wearable computing device 130 determines that a management message is received from the mobile computing device 110 in decision block 702, the method 700 advances to decision block 704.

In decision block 704, the wearable computing device 130 determines whether the management message received from the mobile computing device 110 is a control message. That is, the wearable computing device 130 determines whether the received management message includes one or more functionality instructions (or commands) and/or one or more power state instructions (or commands) for causing the wearable computing device 130 to adjust (e.g., modify, reconfigure, etc.) its current functionality and/or power state. As discussed, in some embodiments, the control message may include a functionality enable instruction to cause the wearable computing device 130 to initialize a function, a functionality disable instruction to cause the wearable computing device 130 to terminate a function, a working power state instruction to cause the wearable computing device 130 to enter an operational mode, a standby power state instruction to cause the wearable computing device 130 to enter a sleep mode, a suspend to disk power state instruction to cause the wearable computing device 130 to enter a hibernate mode, and/or a shutdown power state instruction to cause the wearable computing device 130 to enter a powered down mode. It should be appreciated that a control message received from the mobile computing device 110 may include any other instruction or command to cause the wearable computing device 130 to adjust its current functionality and/or power state. If the wearable computing device 130 determines that the management message received from the mobile computing device 110 is a control message in decision block 704, the method 700 advances to block 706 in which the wearable computing device 130 adjusts its current functionality and/or power state based at least in part on the control message. To do so, the wearable computing device 130 executes the functionality and/or power state instruction(s) and/or command(s) included in the control message.

Referring back to decision block 704, if the wearable computing device 130 determines that the management message received from the mobile computing device 110 is not a control message, the method 700 advances to decision block 708. In decision block 708, the wearable computing device 130 determines whether the management message received from the mobile computing device 110 is a notification message. If the wearable computing device 130 determines that the management message received from the mobile computing device 110 is not a notification message, the method 700 loops back to decision block 702 in which the management message is ignored and the wearable computing device 130 determines whether another management message is received from the mobile computing device 110. If, however, the wearable computing device 130 determines that the management message received from the mobile computing device 110 is a notification message in decision block 708, the method 700 subsequently advances to block 710 in which the wearable computing device 130 displays the notification message on a display to indicate to a user that adjustment to the functionality and/or the power state of the wearable computing device 130 is required.

EXAMPLES

Illustrative examples of the technologies disclosed herein are provided below. An embodiment of the technologies may include any one or more, and any combination of, the examples described below.

Example 1 includes a mobile computing device for context-based management of a wearable computing device, the mobile computing device including a context sensor to generate first sensor data indicative of a first location context of the mobile computing device; a sensor data analysis module to (i) receive second sensor data from the wearable computing device, wherein the second sensor data is indicative of a second location context of the wearable computing device, (ii) fuse the first sensor data and the second sensor data to generate fused sensor data, and (iii) determine a context of the wearable computing device based on the fused sensor data; and a remote device management module to (i) determine whether an adjustment to functionality of the wearable computing device is required based on the determined context and (ii) manage the functionality of the wearable computing device in response to a determination that the adjustment to the functionality is required.

Example 2 includes the subject matter of Example 1, and wherein to receive the second sensor data indicative of the second location context of the wearable computing device includes to periodically receive the second sensor data transmitted by the wearable computing device.

Example 3 includes the subject matter of any of Examples 1 and 2, and wherein the sensor data analysis module is further to transmit an interrogation signal to the wearable computing device, and wherein to receive the second sensor data indicative of the second location context of the wearable computing device includes to receive the second sensor data from the wearable computing device in response to the interrogation signal.

Example 4 includes the subject matter of any of Examples 1-3, and wherein to manage the functionality of the wearable computing device includes to transmit a control message to the wearable computing device to adjust the functionality of the wearable computing device.

Example 5 includes the subject matter of any of Examples 1-4, and wherein to manage the functionality of the wearable computing device includes to transmit a notification message to the wearable computing device to be displayed, wherein the notification message indicates that adjustment to the functionality of the wearable computing device is required.

Example 6 includes the subject matter 1-5, and wherein to fuse the first sensor data and the second sensor data includes to combine the first sensor data and the second sensor data via at least one of a Kalman filter, a decision tree, or a hidden Markov model.

Example 7 includes the subject matter of any of Examples 1-6, and wherein to determine the context of the wearable computing device includes to determine, based on the fused sensor data, whether the wearable computing device is located in a reference location.

Example 8 includes the subject matter of any of Examples 1-7, and wherein to determine whether the wearable computing device is located in the reference location includes to determine, based on the fused sensor data, whether the wearable computing device is located in a reference physical location.

Example 9 includes the subject matter of any of Examples 1-8, and wherein to determine whether the wearable computing device is located in the reference location includes to determine, based on the fused sensor data, whether the wearable computing device is located in a reference semantic location.

Example 10 includes the subject matter of any of Examples 1-9, and wherein the reference semantic location includes at least one of a home, an office, a store, a fitness facility, an automobile, a park, a living room, a kitchen, a conference room, a cubicle, a cafeteria, a hiking trail, a highway, or a city street.

Example 11 includes the subject matter of any of Examples 1-10, and wherein to determine the context of the wearable computing device includes to determine, based on the fused sensor data, whether the wearable computing device is located within a reference distance to the mobile computing device.

Example 12 includes the subject matter of any of Examples 1-11, and wherein the sensor data analysis module is further to receive third sensor data from a different wearable computing device, wherein the third sensor data is indicative of a third location context of the different wearable computing device, and wherein to fuse the first sensor data and the second sensor data to generate the fused sensor data includes to fuse the third sensor data received from the different wearable computing device with the first sensor data and the second sensor data to generate the fused sensor data.

Example 13 includes the subject matter of any of Examples 1-12, and wherein to determine the context of the wearable computing device includes to determine, based on the fused sensor data, whether the wearable computing device is located in a first reference location; determine, based on the fused sensor data, whether the mobile computing device is located in a second reference location; and determine, based on the fused sensor data, whether the different wearable computing device is located in a third reference location.

Example 14 includes the subject matter of any of Examples 1-13, and wherein the context sensor is further to generate fourth sensor data indicative of a relational context between the mobile computing device, the wearable computing device, and the different wearable computing device, and wherein to determine the context of the wearable computing device includes to determine, based on the fused sensor data and the fourth sensor data, whether the wearable computing device is (i) located within a first reference distance to the mobile computing device and (ii) located within a second reference distance to the different wearable computing device.

Example 15 includes the subject matter of any of Examples 1-14, and wherein the context sensor is further to generate fourth sensor data indicative of (i) a first wireless signal strength between the mobile computing device and the wearable computing device and (ii) a second wireless signal strength between the mobile computing device and a different wearable computing device; wherein the sensor data analysis module is further to receive fifth sensor data from the wearable computing device, wherein the fifth sensor data is indicative of a third wireless signal strength between the wearable computing device and the different wearable computing device; wherein to fuse the first sensor data, the second sensor data, and the third sensor data to generate the fused sensor data includes to fuse the fourth sensor data generated by the mobile computing device and the fifth sensor data received from the wearable computing device with the first sensor data, the second sensor data, and the third sensor data to generate the fused sensor data; and wherein to determine the context of the wearable computing device includes to determine, based on the fused sensor data, whether the wearable computing device is (i) located within a first reference distance to the mobile computing device and (ii) located within a second reference distance to the different wearable computing device.

Example 16 includes the subject matter of any of Examples 1-15, and wherein the remote device management module is further to (i) determine whether a separate adjustment to a power state of the wearable computing device is required based on the determined context and (ii) manage the power state of the wearable computing device in response to a determination that the separate adjustment to the power state is required.

Example 17 includes the subject matter of any of Examples 1-16, and wherein to determine whether the adjustment to the functionality of the wearable computing device is required and to determine whether the separate adjustment to the power state of the wearable computing device is required includes to compare the determined context to one or more rules of a context policy database, each of the one or more rules of the context policy database defines at least one of a functionality adjustment or a power state adjustment to be applied to the wearable computing device based on a different determined context of the wearable computing device.

Example 18 includes the subject matter of any of Examples 1-17, and wherein the functionality adjustment includes at least one of a functionality enable instruction to cause the wearable computing device to initialize a function or a functionality disable instruction to cause the wearable computing device to terminate a function.

Example 19 includes the subject matter of any of Examples 1-18, and wherein the power state adjustment includes at least one of a working power state instruction to cause the wearable computing device to enter an operational mode, a standby power state instruction to cause the wearable computing device to enter a sleep mode, a suspend to disk power state instruction to cause the wearable computing device to enter a hibernate mode, or a shutdown power state instruction to cause the wearable computing device to enter a powered down mode.

Example 20 includes a method for context-based management of a wearable computing device, the method including generating, by a mobile computing device, first sensor data indicative of a first location context of the mobile computing device; receiving, by the mobile computing device and from the wearable computing device, second sensor data indicative of a second location context of the wearable computing device; fusing, by the mobile computing device, the first sensor data and the second sensor data to generate fused sensor data; determining, by the mobile computing device, a context of the wearable computing device based on the fused sensor data; determining, by the mobile computing device, whether an adjustment to functionality of the wearable computing device is required based on the determined context; and managing, by the mobile computing device, the functionality of the wearable computing device in response to a determination that the adjustment to the functionality is required.

Example 21 includes the subject matter of Example 20, and wherein receiving the second sensor data indicative of the second location context of the wearable computing device includes periodically receiving the second sensor data transmitted by the wearable computing device.

Example 22 includes the subject matter of any of Examples 20 and 21, and further including transmitting, by the mobile computing device, an interrogation signal to the wearable computing device, and wherein receiving the second sensor data indicative of the second location context of the wearable computing device includes receiving the second sensor data from the wearable computing device in response to the interrogation signal.

Example 23 includes the subject matter of any of Examples 20-22, and wherein managing the functionality of the wearable computing device includes transmitting a control message to the wearable computing device to adjust the functionality of the wearable computing device.

Example 24 includes the subject matter of any of Examples 20-23, and wherein managing the functionality of the wearable computing device includes transmitting a notification message to the wearable computing device to be displayed, wherein the notification message indicates that adjustment to the functionality of the wearable computing device is required.

Example 25 includes the subject matter of any of Examples 20-24, and wherein fusing the first sensor data and the second sensor data includes combining the first sensor data and the second sensor data via at least one of a Kalman filter, a decision tree, or a hidden Markov model.

Example 26 includes the subject matter of any of Examples 20-25, and wherein determining the context of the wearable computing device includes determining, based on the fused sensor data, whether the wearable computing device is located in a reference location.

Example 27 includes the subject matter of any of Examples 20-26, and wherein determining whether the wearable computing device is located in the reference location includes determining, based on the fused sensor data, whether the wearable computing device is located in a reference physical location.

Example 28 includes the subject matter of any of Examples 20-27, and wherein determining whether the wearable computing device is located in the reference location includes determining, based on the fused sensor data, whether the wearable computing device is located in a reference semantic location.

Example 29 includes the subject matter of any of Examples 20-28, and wherein the reference semantic location includes at least one of a home, an office, a store, a fitness facility, an automobile, a park, a living room, a kitchen, a conference room, a cubicle, a cafeteria, a hiking trail, a highway, or a city street.

Example 30 includes the subject matter of any of Examples 20-29, and wherein determining the context of the wearable computing device includes determining, based on the fused sensor data, whether the wearable computing device is located within a reference distance to the mobile computing device.

Example 31 includes the subject matter of any of Examples 20-30, and further including receiving, by the mobile computing device and from a different wearable computing device, third sensor data indicative of a third location context of the different wearable computing device, and wherein fusing the first sensor data and the second sensor data to generate the fused sensor data includes fusing the third sensor data received from the different wearable computing device with the first sensor data and the second sensor data to generate the fused sensor data.

Example 32 includes the subject matter of any of Examples 20-31, and wherein determining the context of the wearable computing device includes (i) determining, based on the fused sensor data, whether the wearable computing device is located in a first reference location, (ii) determining, based on the fused sensor data, whether the mobile computing device is located in a second reference location, and (iii) determining, based on the fused sensor data, whether the different wearable computing device is located in a third reference location.

Example 33 includes the subject matter of any of Examples 20-32, and further including generating, by the mobile computing device, fourth sensor data indicative of a relational context between the mobile computing device, the wearable computing device, and the different wearable computing device, and wherein determining the context of the wearable computing device includes determining, based on the fused sensor data and the fourth sensor data, whether the wearable computing device is (i) located within a first reference distance to the mobile computing device and (ii) located within a second reference distance to the different wearable computing device.

Example 34 includes the subject matter of any of Examples 20-33, and further including generating, by the mobile computing device, fourth sensor data indicative of (i) a first wireless signal strength between the mobile computing device and the wearable computing device and (ii) a second wireless signal strength between the mobile computing device and a different wearable computing device; and receiving, by the mobile computing device and from the wearable computing device, fifth sensor data indicative of a third wireless signal strength between the wearable computing device and the different wearable computing device, and wherein fusing the first sensor data, the second sensor data, and the third sensor data to generate the fused sensor data includes fusing the fourth sensor data generated by the mobile computing device and the fifth sensor data received from the wearable computing device with the first sensor data, the second sensor data, and the third sensor data to generate the fused sensor data, and wherein determining the context of the wearable computing device includes determining, based on the fused sensor data, whether the wearable computing device is (i) located within a first reference distance to the mobile computing device and (ii) located within a second reference distance to the different wearable computing device.

Example 35 includes the subject matter of any of Examples 20-34, and further including determining, by the mobile computing device, whether a separate adjustment to a power state of the wearable computing device is required based on the determined context; and managing, by the mobile computing device, the power state of the wearable computing device in response to a determination that the separate adjustment to the power state is required.

Example 36 includes the subject matter of any of Examples 20-35, and wherein determining whether the adjustment to the functionality of the wearable computing device is required and determining whether the separate adjustment to the power state of the wearable computing device is required includes comparing the determined context to one or more rules of a context policy database, each of the one or more rules of the context policy database defines at least one of a functionality adjustment or a power state adjustment to be applied to the wearable computing device based on a different determined context of the wearable computing device.

Example 37 includes the subject matter of any of Examples 20-36, and wherein the functionality adjustment includes at least one of a functionality enable instruction to cause the wearable computing device to initialize a function or a functionality disable instruction to cause the wearable computing device to terminate a function.

Example 38 includes the subject matter of any of Examples 20-37, and wherein the power state adjustment includes at least one of a working power state instruction to cause the wearable computing device to enter an operational mode, a standby power state instruction to cause the wearable computing device to enter a sleep mode, a suspend to disk power state instruction to cause the wearable computing device to enter a hibernate mode, or a shutdown power state instruction to cause the wearable computing device to enter a powered down mode.

Example 39 includes a mobile computing device for context-based management of a wearable computing device, the mobile computing device including a processor; and a memory having stored therein a plurality of instructions that when executed by the processor cause the mobile computing device to perform the method of any of Examples 20-38.

Example 40 includes one or more machine-readable media having a plurality of instructions stored thereon that in response to being executed result in a mobile computing device performing the method of any of Examples 20-38.

Example 41 includes a mobile computing device for context-based management of a wearable computing device, the mobile computing device including means for generating first sensor data indicative of a first location context of the mobile computing device; means for receiving second sensor data from the wearable computing device, wherein the second sensor data is indicative of a second location context of the wearable computing device; means for fusing the first sensor data and the second sensor data to generate fused sensor data; means for determining a context of the wearable computing device based on the fused sensor data; means for determining whether an adjustment to functionality of the wearable computing device is required based on the determined context; and means for managing the functionality of the wearable computing device in response to a determination that the adjustment to the functionality is required.

Example 42 includes the subject matter of Example 41, and wherein the means for receiving the second sensor data indicative of the second location context of the wearable computing device includes means for periodically receiving the second sensor data transmitted by the wearable computing device.

Example 43 includes the subject matter of any of Examples 41 and 42, and further including means for transmitting an interrogation signal to the wearable computing device, and wherein the means for receiving the second sensor data indicative of the second location context of the wearable computing device includes means for receiving the second sensor data from the wearable computing device in response to the interrogation signal.

Example 44 includes the subject matter of any of Examples 41-43, and wherein the means for managing the functionality of the wearable computing device includes means for transmitting a control message to the wearable computing device to adjust the functionality of the wearable computing device.

Example 45 includes the subject matter of any of Examples 41-44, and wherein the means for managing the functionality of the wearable computing device includes means for transmitting a notification message to the wearable computing device to be displayed, wherein the notification message indicates that adjustment to the functionality of the wearable computing device is required.

Example 46 includes the subject matter of any of Examples 41-45, and wherein the means for fusing the first sensor data and the second sensor data includes means for combining the first sensor data and the second sensor data via at least one of a Kalman filter, a decision tree, or a hidden Markov model.

Example 47 includes the subject matter of any of Examples 41-46, and wherein the means for determining the context of the wearable computing device includes means for determining, based on the fused sensor data, whether the wearable computing device is located in a reference location.

Example 48 includes the subject matter of any of Examples 41-47, and wherein the means for determining whether the wearable computing device is located in the reference location includes means for determining, based on the fused sensor data, whether the wearable computing device is located in a reference physical location.

Example 49 includes the subject matter of any of Examples 41-48, and wherein the means for determining whether the wearable computing device is located in the reference location includes means for determining, based on the fused sensor data, whether the wearable computing device is located in a reference semantic location.

Example 50 includes the subject matter of any of Examples 41-49, and wherein the reference semantic location includes at least one of a home, an office, a store, a fitness facility, an automobile, a park, a living room, a kitchen, a conference room, a cubicle, a cafeteria, a hiking trail, a highway, or a city street.

Example 51 includes the subject matter of any of Examples 41-50, and wherein the means for determining the context of the wearable computing device includes means for determining, based on the fused sensor data, whether the wearable computing device is located within a reference distance to the mobile computing device.

Example 52 includes the subject matter of any of Examples 41-51, and further including means for receiving third sensor data from a different wearable computing device, wherein the third sensor data is indicative of a third location context of the different wearable computing device, and wherein the means for fusing the first sensor data and the second sensor data to generate the fused sensor data includes means for fusing the third sensor data received from the different wearable computing device with the first sensor data and the second sensor data to generate the fused sensor data.

Example 53 includes the subject matter of any of Examples 41-52, and wherein the means for determining the context of the wearable computing device includes (i) means for determining, based on the fused sensor data, whether the wearable computing device is located in a first reference location, (ii) means for determining, based on the fused sensor data, whether the mobile computing device is located in a second reference location, and (iii) means for determining, based on the fused sensor data, whether the different wearable computing device is located in a third reference location.

Example 54 includes the subject matter of any of Examples 41-53, and further including means for generating fourth sensor data indicative of a relational context between the mobile computing device, the wearable computing device, and the different wearable computing device, and wherein the means for determining the context of the wearable computing device includes means for determining, based on the fused sensor data and the fourth sensor data, whether the wearable computing device is (i) located within a first reference distance to the mobile computing device and (ii) located within a second reference distance to the different wearable computing device.

Example 55 includes the subject matter of any of Examples 41-54, and further including means for generating fourth sensor data indicative of (i) a first wireless signal strength between the mobile computing device and the wearable computing device and (ii) a second wireless signal strength between the mobile computing device and a different wearable computing device; and means for receiving fifth sensor data from the wearable computing device, wherein the fifth sensor data is indicative of a third wireless signal strength between the wearable computing device and the different wearable computing device, and wherein the means for fusing the first sensor data, the second sensor data, and the third sensor data to generate the fused sensor data includes means for fusing the fourth sensor data generated by the mobile computing device and the fifth sensor data received from the wearable computing device with the first sensor data, the second sensor data, and the third sensor data to generate the fused sensor data, and wherein the means for determining the context of the wearable computing device includes means for determining, based on the fused sensor data, whether the wearable computing device is (i) located within a first reference distance to the mobile computing device and (ii) located within a second reference distance to the different wearable computing device.

Example 56 includes the subject matter of any of Examples 41-55, and further including means for determining whether a separate adjustment to a power state of the wearable computing device is required based on the determined context; and means for managing the power state of the wearable computing device in response to a determination that the separate adjustment to the power state is required.

Example 57 includes the subject matter of any of Examples 41-56, and wherein the means for determining whether the adjustment to the functionality of the wearable computing device is required and the means for determining whether the separate adjustment to the power state of the wearable computing device is required includes means for comparing the determined context to one or more rules of a context policy database, each of the one or more rules of the context policy database defines at least one of a functionality adjustment or a power state adjustment to be applied to the wearable computing device based on a different determined context of the wearable computing device.

Example 58 includes the subject matter of any of Examples 41-57, and wherein the functionality adjustment includes at least one of a functionality enable instruction to cause the wearable computing device to initialize a function or a functionality disable instruction to cause the wearable computing device to terminate a function.

Example 59 includes the subject matter of any of Examples 41-58, and wherein the power state adjustment includes at least one of a working power state instruction to cause the wearable computing device to enter an operational mode, a standby power state instruction to cause the wearable computing device to enter a sleep mode, a suspend to disk power state instruction to cause the wearable computing device to enter a hibernate mode, or a shutdown power state instruction to cause the wearable computing device to enter a powered down mode.

Example 60 includes a mobile computing device to determine a location of the mobile computing device, the mobile computing device including a context sensor to generate first sensor data indicative of a first location context of the mobile computing device; a sensor data analysis module to (i) receive second sensor data from a wearable computing device, wherein the second sensor data is indicative of a second location context of the wearable computing device, (ii) fuse the first sensor data and the second sensor data to generate fused sensor data, and (iii) determine the location of the mobile computing device based on the fused sensor data.

Example 61 includes the subject matter of Example 60, and wherein to determine the location of the mobile computing device includes to determine a physical location of the mobile computing device based on the fused sensor data.

Example 62 includes the subject matter of any of Examples 60 and 61, and wherein to determine the location of the mobile computing device includes to determine a semantic location of the mobile computing device based on the fused sensor data.

Example 63 includes the subject matter of any of Examples 60-62, and wherein the semantic location of the mobile computing device includes at least one of a home, an office, a store, a fitness facility, an automobile, a park, a living room, a kitchen, a conference room, a cubicle, a cafeteria, a hiking trail, a highway, or a city street.

Example 64 includes the subject matter of any of Examples 60-63, and wherein the sensor data analysis module is further to receive third sensor data from a different wearable computing device, wherein the third sensor data is indicative of a third location context of the different wearable computing device, and wherein to fuse the first sensor data and the second sensor data to generate the fused sensor data includes to fuse the third sensor data received from the different wearable computing device with the first sensor data and the second sensor data to generate the fused sensor data.

Example 65 includes a method for determining a location of a mobile computing device, the method including generating, by the mobile computing device, first sensor data indicative of a first location context of the mobile computing device; receiving, by the mobile computing device and from a wearable computing device, second sensor data indicative of a second location context of the wearable computing device; fusing, by the mobile computing device, the first sensor data and the second sensor data to generate fused sensor data; and determining, by the mobile computing device, the location of the mobile computing device based on the fused sensor data.

Example 66 includes the subject matter of Example 65, and wherein determining the location of the mobile computing device includes determining a physical location of the mobile computing device based on the fused sensor data.

Example 67 includes the subject matter of any of Examples 65 and 66, and wherein determining the location of the mobile computing device includes determining a semantic location of the mobile computing device based on the fused sensor data.

Example 68 includes the subject matter of any of Examples 65-67, and wherein the semantic location of the mobile computing device includes at least one of a home, an office, a store, a fitness facility, an automobile, a park, a living room, a kitchen, a conference room, a cubicle, a cafeteria, a hiking trail, a highway, or a city street.

Example 69 includes the subject matter of any of Examples 65-68, and further including receiving, by the mobile computing device and from a different wearable computing device, third sensor data indicative of a third location context of the different wearable computing device, and wherein fusing the first sensor data and the second sensor data to generate the fused sensor data includes fusing the third sensor data received from the different wearable computing device with the first sensor data and the second sensor data to generate the fused sensor data.

Example 70 includes a mobile computing device to determine a location of the mobile computing device, the mobile computing device including a processor; and a memory having stored therein a plurality of instructions that when executed by the processor cause the mobile computing device to perform the method of any of Examples 65-69.

Example 71 includes one or more machine-readable media having a plurality of instructions stored thereon that in response to being executed result in a mobile computing device performing the method of any of Examples 65-69.

Example 72 includes a mobile computing device to determine a location of the mobile computing device, the mobile computing device including means for generating first sensor data indicative of a first location context of the mobile computing device; means for receiving second sensor data from a wearable computing device, wherein the second sensor data is indicative of a second location context of the wearable computing device; means for fusing the first sensor data and the second sensor data to generate fused sensor data; and means for determining the location of the mobile computing device based on the fused sensor data.

Example 73 includes the subject matter of Example 72, and wherein the means for determining the location of the mobile computing device includes means for determining a physical location of the mobile computing device based on the fused sensor data.

Example 74 includes the subject matter of any of Examples 72 and 73, and wherein the means for determining the location of the mobile computing device includes means for determining a semantic location of the mobile computing device based on the fused sensor data.

Example 75 includes the subject matter of any of Examples 72-74, and wherein the semantic location of the mobile computing device includes at least one of a home, an office, a store, a fitness facility, an automobile, a park, a living room, a kitchen, a conference room, a cubicle, a cafeteria, a hiking trail, a highway, or a city street.

Example 76 includes the subject matter of any of Examples 72-75, and further including means for receiving third sensor data from a different wearable computing device, wherein the third sensor data is indicative of a third location context of the different wearable computing device, and wherein the means for fusing the first sensor data and the second sensor data to generate the fused sensor data includes means for fusing the third sensor data received from the different wearable computing device with the first sensor data and the second sensor data to generate the fused sensor data.

Example 77 includes a wearable computing device for context-based management, the wearable computing device including a local context sensor to generate sensor data indicative of a location context of the wearable computing device; a remote device synchronization module to transmit the sensor data to a mobile computing device, wherein the sensor data to be fused with remote sensor data to generate fused sensor data for remote determination of a context of the wearable computing device; and a local device management module to (i) determine whether a management message generated based on the remotely determined context of the wearable computing device is received from the mobile computing device, (ii) determine, in response to a determination that the management message is received from the mobile computing device, whether the received management message is a control message, and (iii) adjust the functionality of the wearable computing device in response to a determination that the management message received from the mobile computing device is a control message.

Example 78 includes the subject matter of Example 77, and wherein the local device management module is further to (i) determine, in response to the determination that the management message is received from the mobile computing device, whether the received management message is a notification message and (ii) display the notification message to indicate that adjustment to the functionality of the wearable computing device is required.

Example 79 includes the subject matter of any of Examples 77 and 78, and wherein to transmit the sensor data indicative of the location context of the wearable computing device includes to periodically transmit the sensor data to the mobile computing device.

Example 80 includes the subject matter of any of Examples 77-79, and wherein the remote device synchronization module is further to receive an interrogation signal from the mobile computing device, and wherein to transmit the sensor data indicative of the location context of the wearable computing device includes to transmit the sensor data to the mobile computing device in response to the interrogation signal.

Example 81 includes the subject matter of any of Examples 77-80, and further including a local data storage to locally store the sensor data generated by the local context sensor, wherein to transmit the sensor data indicative of the location context of the wearable computing device includes to (i) retrieve the sensor data from the local data storage and (ii) transmit the sensor data to the mobile computing device.

Example 82 includes the subject matter of any of Examples 77-81, and wherein the sensor data generated by the local context sensor includes first sensor data; wherein the local context sensor is further to generate second sensor data indicative of a wireless signal strength between the wearable computing device and a different wearable computing device; and wherein the remote device synchronization module is further to transmit the second sensor data to the mobile computing device, wherein the second sensor data to be fused with the first sensor data and the remote sensor data to generate the fused sensor data for remote determination of the context of the wearable computing device.

Example 83 includes the subject matter of any of Examples 77-82, and wherein the control message includes at least one of a functionality enable instruction to cause the wearable computing device to initialize a function, a functionality disable instruction to cause the wearable computing device to terminate a function, a working power state instruction to cause the wearable computing device to enter an operational mode, a standby power state instruction to cause the wearable computing device to enter a sleep mode, a suspend to disk power state instruction to cause the wearable computing device to enter a hibernate mode, or a shutdown power state instruction to cause the wearable computing device to enter a powered down mode.

Example 84 includes the subject matter of any of Examples 77-83, and wherein the local device management module is further to manage a power state of the wearable computing device in response to the received control message including at least one of the working power state instruction, the standby power state instruction, the suspend to disk power state instruction, or the shutdown power state instruction.

Example 85 includes a method for context-based management of a wearable computing device, the method including generating, by a local context sensor of the wearable computing device, sensor data indicative of a location context of the wearable computing device; transmitting, by the wearable computing device, the sensor data to a mobile computing device, wherein the sensor data to be fused with remote sensor data to generate fused sensor data for remote determination of a context of the wearable computing device; receiving, by the wearable computing device and from the mobile computing device, a management message generated based on the remotely determined context of the wearable computing device; determining, by the wearable computing device and in response to receiving the management message from the mobile computing device, whether the received management message is a control message; and adjusting, by the wearable computing device, the functionality of the wearable computing device in response to a determination that the management message received from the mobile computing device is a control message.

Example 86 includes the subject matter of Example 85, and further including determining, by the wearable computing device and in response to receiving the management message from the mobile computing device, whether the received management message is a notification message; and displaying, by the wearable computing device, the notification message to indicate that adjustment to the functionality of the wearable computing device is required.

Example 87 includes the subject matter of any of Examples 85 and 86, and wherein transmitting the sensor data indicative of the location context of the wearable computing device includes periodically transmitting the sensor data to the mobile computing device.

Example 88 includes the subject matter of any of Examples 85-87, and further including receiving, by the wearable computing device, an interrogation signal from the mobile computing device, and wherein transmitting the sensor data indicative of the location context of the wearable computing device includes transmitting the sensor data to the mobile computing device in response to the interrogation signal.

Example 89 includes the subject matter of any of Examples 85-88, and further including locally storing, by the wearable computing device, the sensor data generated by the local context sensor in a local data storage of the wearable computing device, and wherein transmitting the sensor data indicative of the location context of the wearable computing device includes (i) retrieving the sensor data from the local data storage and (ii) transmitting the sensor data to the mobile computing device.

Example 90 includes the subject matter of any of Examples 85-89, and wherein the sensor data generated by the local context sensor includes first sensor data; and further including generating, by the local context sensor of the wearable computing device, second sensor data indicative of a wireless signal strength between the wearable computing device and a different wearable computing device, and transmitting, by the wearable computing device, the second sensor data to the mobile computing device, wherein the second sensor data to be fused with the first sensor data and the remote sensor data to generate the fused sensor data for remote determination of the context of the wearable computing device.

Example 91 includes the subject matter of any of Examples 85-90, and wherein the control message includes at least one of a functionality enable instruction to cause the wearable computing device to initialize a function, a functionality disable instruction to cause the wearable computing device to terminate a function, a working power state instruction to cause the wearable computing device to enter an operational mode, a standby power state instruction to cause the wearable computing device to enter a sleep mode, a suspend to disk power state instruction to cause the wearable computing device to enter a hibernate mode, or a shutdown power state instruction to cause the wearable computing device to enter a powered down mode.

Example 92 includes the subject matter of any of Examples 85-91, and by the wearable computing device, a power state of the wearable computing device in response to the received control message including at least one of the working power state instruction, the standby power state instruction, the suspend to disk power state instruction, or the shutdown power state instruction.

Example 93 includes a wearable computing device for context-based management, the wearable computing device including a processor; and a memory having stored therein a plurality of instructions that when executed by the processor cause the wearable computing device to perform the method of any of Examples 85-92.

Example 94 includes one or more machine-readable media having a plurality of instructions stored thereon that in response to being executed result in a wearable computing device performing the method of any of Examples 85-92.

Example 95 includes a wearable computing device for context-based management, the wearable computing device including means for generating sensor data indicative of a location context of the wearable computing device; means for transmitting the sensor data to a mobile computing device, wherein the sensor data to be fused with remote sensor data to generate fused sensor data for remote determination of a context of the wearable computing device; means for receiving, from the mobile computing device, a management message generated based on the remotely determined context of the wearable computing device; means for determining, in response to receiving the management message from the mobile computing device, whether the received management message is a control message; and means for adjusting the functionality of the wearable computing device in response to a determination that the management message received from the mobile computing device is a control message.

Example 96 includes the subject matter of Example 95, and further including means for determining, in response to receiving the management message from the mobile computing device, whether the received management message is a notification message; and means for displaying the notification message to indicate that adjustment to the functionality of the wearable computing device is required.

Example 97 includes the subject matter of any of Examples 95 and 96, and wherein the means for transmitting the sensor data indicative of the location context of the wearable computing device includes means for periodically transmitting the sensor data to the mobile computing device.

Example 98 includes the subject matter of any of Examples 95-97, and further including means for receiving an interrogation signal from the mobile computing device, and wherein the means for transmitting the sensor data indicative of the location context of the wearable computing device includes means for transmitting the sensor data to the mobile computing device in response to the interrogation signal.

Example 99 includes the subject matter of any of Examples 95-98, and further including means for locally storing the sensor data generated by the wearable computing device in a local data storage of the wearable computing device, and wherein the means for transmitting the sensor data indicative of the location context of the wearable computing device includes (i) means for retrieving the sensor data from the local data storage and (ii) means for transmitting the sensor data to the mobile computing device.

Example 100 includes the subject matter of any of Examples 95-99, and wherein the sensor data generated by the local context sensor includes first sensor data; and further including (i) means for generating second sensor data indicative of a wireless signal strength between the wearable computing device and a different wearable computing device, and (ii) means for transmitting the second sensor data to the mobile computing device, wherein the second sensor data to be fused with the first sensor data and the remote sensor data to generate the fused sensor data for remote determination of the context of the wearable computing device.

Example 101 includes the subject matter of any of Examples 95-100, and wherein the control message includes at least one of a functionality enable instruction to cause the wearable computing device to initialize a function, a functionality disable instruction to cause the wearable computing device to terminate a function, a working power state instruction to cause the wearable computing device to enter an operational mode, a standby power state instruction to cause the wearable computing device to enter a sleep mode, a suspend to disk power state instruction to cause the wearable computing device to enter a hibernate mode, or a shutdown power state instruction to cause the wearable computing device to enter a powered down mode.

Example 102 includes the subject matter of any of Examples 95-101, and further including means for managing a power state of the wearable computing device in response to the received control message including at least one of the working power state instruction, the standby power state instruction, the suspend to disk power state instruction, or the shutdown power state instruction.

The invention claimed is:
1. A wearable computing device for context-based management, the wearable computing device comprising:
   a local context sensor to generate sensor data indicative of a location context of the wearable computing device;
   transmitter to transmit the sensor data to a mobile computing device, the sensor data to be fused with remote sensor data to generate fused sensor data for remote determination of a context of the wearable computing device; and local device circuitry to (i) determine whether a management message generated based on the remotely determined context of the wearable computing device has been received from the mobile computing device, (ii) determine, in response to a determination that the management message has been received from the mobile computing device, whether the received management message is a control message, and (iii) adjust the functionality of the wearable computing device in response to a determination that the management message received from the mobile computing device is a control message.

2. The wearable computing device of claim 1, wherein the local device circuitry is to (i) determine, in response to the determination that the management message has been received from the mobile computing device, whether the received management message is a notification message and (ii) display the notification message to indicate that adjustment to the functionality of the wearable computing device is required.

3. The wearable computing device of claim 1, wherein the transmitter is to transmit the sensor data indicative of the location context of the wearable computing device periodically to the mobile computing device.

4. The wearable computing device of claim 1, wherein the transmitter is to receive an interrogation signal from the mobile computing device and transmit the sensor data to the mobile computing device in response to the interrogation signal.

5. The wearable computing device of claim 1, further including a local data storage to locally store the sensor data generated by the local context sensor, wherein the sensor data indicative of the location context of the wearable computing device is from the local data storage.

6. The wearable computing device of claim 1, wherein the sensor data generated by the local context sensor includes first sensor data;
wherein the local context sensor is to generate second sensor data indicative of a wireless signal strength between the wearable computing device and a different wearable computing device; and
wherein the transmitter is to transmit the second sensor data to the mobile computing device, the second sensor data to be fused with the first sensor data and the remote sensor data to generate the fused sensor data for remote determination of the context of the wearable computing device.

7. The wearable computing device of claim 1, wherein the control message includes at least one of a functionality enable instruction to cause the wearable computing device to initialize a function, a functionality disable instruction to cause the wearable computing device to terminate a function, a working power state instruction to cause the wearable computing device to enter an operational mode, a standby power state instruction to cause the wearable computing device to enter a sleep mode, a suspend to disk power state instruction to cause the wearable computing device to enter a hibernate mode, or a shutdown power state instruction to cause the wearable computing device to enter a powered down mode.

8. The wearable computing device of claim 7, wherein the local device circuitry is to manage a power state of the wearable computing device in response to the control message including at least one of the working power state instruction, the standby power state instruction, the suspend to disk power state instruction, or the shutdown power state instruction.

9. A method for context-based management of a wearable computing device, the method comprising:
transmitting sensor data, from the wearable computing device, to a mobile computing device, the sensor data to be generated by a local context sensor of the wearable computing device, the sensor data indicative of a location context of the wearable computing device, the sensor data to be fused with remote sensor data to generate fused sensor data for remote determination of a context of the wearable computing device;
receiving, by the wearable computing device and from the mobile computing device, a management message generated based on the remotely determined context of the wearable computing device;
determining, by the wearable computing device and in response to receiving the management message from the mobile computing device, whether the received management message is a control message; and
adjusting, by the wearable computing device, the functionality of the wearable computing device in response to a determination that the management message received from the mobile computing device is a control message.

10. The method of claim 9, further including:
determining, by the wearable computing device and in response to receiving the management message from the mobile computing device, whether the received management message is a notification message; and
displaying, by the wearable computing device, the notification message to indicate that adjustment to the functionality of the wearable computing device is required.

11. The method of claim 9, wherein the transmitting of the sensor data indicative of the location context of the wearable computing device includes periodically transmitting the sensor data to the mobile computing device.

12. The method of claim 9, further including receiving, by the wearable computing device, an interrogation signal from the mobile computing device,
wherein the transmitting of the sensor data indicative of the location context of the wearable computing device includes transmitting the sensor data to the mobile computing device in response to the interrogation signal.

13. The method of claim 9, further including locally storing, by the wearable computing device, the sensor data generated by the local context sensor in a local data storage of the wearable computing device,
wherein the transmitting of the sensor data indicative of the location context of the wearable computing device includes (i) retrieving the sensor data from the local data storage and (ii) transmitting the sensor data to the mobile computing device.

14. The method of claim 9, wherein the sensor data generated by the local context sensor includes first sensor data; and further including transmitting, by the wearable computing device, second sensor data to the mobile computing device, the second sensor data to be generated by the local context sensor of the wearable computing device, the second sensor data indicative of a wireless signal strength between the wearable computing device and a different wearable computing device, the second sensor data to be fused with the first sensor data and the remote sensor data to generate the fused sensor data for remote determination of the context of the wearable computing device.

15. The method of claim 9, wherein the control message includes at least one of a functionality enable instruction to cause the wearable computing device to initialize a function, a functionality disable instruction to cause the wearable computing device to terminate a function, a working power state instruction to cause the wearable computing device to enter an operational mode, a standby power state instruction to cause the wearable computing device to enter a sleep mode, a suspend to disk power state instruction to cause the wearable computing device to enter a hibernate mode, or a shutdown power state instruction to cause the wearable computing device to enter a powered down mode.

16. One or more machine-readable memories comprising a plurality of instructions stored thereon that, when executed by a wearable computing device, cause the wearable computing device to:
 transmit sensor data to a mobile computing device, the sensor data indicative of a location context of the wearable computing device, the sensor data to be fused with remote sensor data to generate fused sensor data for remote determination of a context of the wearable computing device;
 determine whether a management message generated based on the remotely determined context of the wearable computing device has been received from the mobile computing device;
 determine, in response to a determination that the management message has been received from the mobile computing device, whether the received management message is a control message; and
 adjust the functionality of the wearable computing device in response to a determination that the management message received from the mobile computing device is a control message.

17. The one or more machine-readable memories of claim 16, wherein the plurality of instructions, when executed, cause the wearable computing device to:
 determine, in response to the determination that the management message has been received from the mobile computing device, whether the received management message is a notification message; and
 display the notification message to indicate that adjustment to the functionality of the wearable computing device is required.

18. The one or more machine-readable memories of claim 16, wherein the plurality of instructions, when executed, cause the wearable computing device to periodically transmit the sensor data to the mobile computing device.

19. The one or more machine-readable memories of claim 16, wherein the plurality of instructions, when executed, cause the wearable computing device to transmit the sensor data to the mobile computing device in response to an interrogation signal.

20. The one or more machine-readable memories of claim 16, wherein the plurality of instructions, when executed, cause the wearable computing device to:
 store the sensor data in a local data storage of the wearable computing device; and
 transmit the sensor data indicative of the location context of the wearable computing device by (i) retrieving the sensor data from the local data storage and (ii) transmitting the sensor data to the mobile computing device.

21. The one or more machine-readable memories of claim 16, wherein the sensor data includes first sensor data; and wherein the plurality of instructions, when executed, cause the wearable computing device to
 transmit second sensor data to the mobile computing device, the second sensor data indicative of a wireless signal strength between the wearable computing device and a different wearable computing device, the second sensor data to be fused with the first sensor data and the remote sensor data to generate the fused sensor data for remote determination of the context of the wearable computing device.

22. The one or more machine-readable memories of claim 16, wherein the control message includes at least one of a functionality enable instruction to cause the wearable computing device to initialize a function, a functionality disable instruction to cause the wearable computing device to terminate a function, a working power state instruction to cause the wearable computing device to enter an operational mode, a standby power state instruction to cause the wearable computing device to enter a sleep mode, a suspend to disk power state instruction to cause the wearable computing device to enter a hibernate mode, or a shutdown power state instruction to cause the wearable computing device to enter a powered down mode.

23. A wearable compute device, the device comprising:
 at least one memory;
 instructions in the device; and
 processor circuitry to execute the instructions to:
  cause transmission of sensor data to a mobile compute device, the sensor data indicative of a location context of the wearable compute device, the sensor data to be fused with remote sensor data to generate fused sensor data to remotely determine a context of the wearable compute device;
  determine whether a management message generated based on the remotely determined context of the wearable compute device has been received from the mobile compute device;
  determine, in response to a determination that the management message has been received from the mobile compute device, whether the received management message is a control message; and
  adjust the functionality of the wearable compute device in response to a determination that the management message received from the mobile compute device is a control message.

24. The wearable compute device of claim 23, wherein the processor circuitry is to:
 determine, in response to the determination that the management message has been received from the mobile compute device, whether the received management message is a notification message; and
 display the notification message to indicate that adjustment to the functionality of the wearable compute device is required.

25. The wearable compute device of claim 23, wherein the processor circuitry is to cause the wearable compute device to periodically transmit the sensor data to the mobile compute device.

26. The wearable compute device of claim 23, wherein the processor circuitry is to e cause the wearable compute device to transmit the sensor data to the mobile compute device in response to an interrogation signal.

27. The wearable compute device of claim 23, wherein the processor circuitry is to cause the wearable compute device to store the sensor data in a local data storage of the wearable compute device.

28. The wearable compute device of claim 23, wherein the sensor data includes first sensor data and the processor circuitry is to cause the wearable compute device to transmit second sensor data to the mobile compute device, the second sensor data indicative of a wireless signal strength between the wearable compute device and a different wearable compute device, the second sensor data to be fused with the first sensor data and the remote sensor data to generate the fused sensor data to remotely determine the context of the wearable compute device.

29. The wearable compute device of claim 23, wherein the control message includes at least one of a functionality enable instruction to cause the wearable compute device to initialize a function, a functionality disable instruction to cause the wearable compute device to terminate a function, a working power state instruction to cause the wearable compute device to enter an operational mode, a standby power state instruction to cause the wearable compute device to enter a sleep mode, a suspend to disk power state instruction to cause the wearable compute device to enter a hibernate mode, or a shutdown power state instruction to cause the wearable compute device to enter a powered down mode.

* * * * *